United States Patent [19]

Kohl et al.

[11] Patent Number: 5,922,720

[45] Date of Patent: Jul. 13, 1999

[54] PIPERAZINOTHIOPYRIDINES FOR THE CONTROL OF HELICOBACTER BACTERIA

[75] Inventors: Bernhard Kohl; Gerhard Grundler; Jorg Senn-Bilfinger, all of Constance, Germany

[73] Assignee: Byk Gulden Lomberg Chemische Fabrik GmbH, Constance, Germany

[21] Appl. No.: 08/765,980

[22] PCT Filed: Jul. 19, 1995

[86] PCT No.: PCT/EP95/02848

§ 371 Date: Jan. 17, 1997

§ 102(e) Date: Jan. 17, 1997

[87] PCT Pub. No.: WO96/02534

PCT Pub. Date: Feb. 1, 1996

[30] Foreign Application Priority Data

Jul. 20, 1994 [CH] Switzerland .............................. 2302/94

[51] Int. Cl.⁶ ........................ A01N 43/60; C07D 401/00; C07D 403/00

[52] U.S. Cl. ........................... 514/255; 514/303; 514/318; 544/360; 544/362; 544/370; 546/188; 546/193

[58] Field of Search ...................................... 514/255, 303, 514/318; 544/360, 362, 370; 546/193, 118

[56] References Cited

U.S. PATENT DOCUMENTS 5,504,082  4/1996  Kawakita et al. .................... 514/234.5

FOREIGN PATENT DOCUMENTS 567643  11/1993  European Pat. Off. .
9324480  12/1993  WIPO .

*Primary Examiner*—Richard L. Raymond
*Assistant Examiner*—Tamthom T. Ngo
*Attorney, Agent, or Firm*—Jacobson, Price, Holman & Stern, PLLC

[57] ABSTRACT

Compounds of formula I are piperazinothiopyridines which are useful for controlling Helicobacter bacteria. They are useful as active compounds for treating diseases based on such bacteria, and are thus useful for making appropriate medicament compositions for administering to humans afflicted with diseases based on or caused by such bacteria.

16 Claims, No Drawings

PIPERAZINOTHIOPYRIDINES FOR THE CONTROL OF HELICOBACTER BACTERIA

FIELD OF APPLICATION OF THE INVENTION

The invention relates to compounds which are intended to be used in the pharmaceutical industry as active compounds for the production of medicaments.

KNOWN TECHNICAL BACKGROUND

European Patent Application 150 586 discloses 2-(pyridylmethylthio- or -sulfinyl)benzimidazoles which can be substituted in the pyridine moiety of the molecule in the 4-position, inter alia, by alkylthio or arylthio radicals. A long-lasting inhibition of gastric acid secretion is indicated for the compounds described. —International Patent Application WO89/03830 describes that the same and also other compounds of similar structure ought to be suitable for the treatment of osteoporosis. —International Patent Application WO92/12976 describes 2-(pyridylmethylthio- or sulfinyl)benzimidazoles substituted in a certain manner, which ought to be active against Helicobacter bacteria and for which it is furthermore disclosed that they ought to be suitable for the prevention and treatment of a whole series of disorders of the stomach. —International Patent Application WO93/24480 describes other 2-(pyridylmethylthio- or -sulfinyl)benzimidazoles substituted in a certain manner, which ought to be active against Helicobacter bacteria.

DESCRIPTION OF THE INVENTION

The inventions relates to compounds of the formula I (see attached formula sheet I), in which R1 is hydrogen, 1–4C-alkyl, 1–4C-alkoxy or halogen,
R2 is hydrogen, 1–4C-alkyl, 1–4C-alkoxy, halogen or trifluoromethyl,
R3 is hydrogen, 1–4C-alkyl, R4-substituted 1–4C-alkyl, 1–4C-alkylcarbonyl, 2–4C-alkenylcarbonyl, halogen-1–4C-alkylcarbonyl, N(R14)R15-1–4C-alkylcarbonyl, di-1–4C-alkylcarbamoyl or 1–4C-alkylsulfonyl,
R4 is hydroxyl, 1–4C-alkoxy, carboxyl, 1–4C-alkoxycarbonyl or —N(R14)R15,
R5 is hydrogen, 1–4C-alkyl or 1–4C-alkoxy,
R6 is an R8- and R9-substituted cyclic system or bicyclic system which is selected from the group consisting of benzene, furan, thiophene, pyrrole, oxazole, isoxazole, thiazole, thiazoline, isothiazole, imidazole, imidazoline, pyrazole, triazole, tetrazole, thiadiazole, thiadiazole-1-oxide, oxadiazole, pyridine, pyridine-N-oxide, pyrimidine, triazine, pyridone, benzimidazole, imidazopyridine, benzothiazole and benzoxazole,
R7 is hydrogen, 1–4C-alkyl or 1–4C-alkoxy,
R8 is hydrogen, 1–4C-alkyl, hydroxyl, 1–4C-alkoxy, halogen, nitro, guanidino, carboxyl, 1–4C-alkoxycarbonyl, R10-substituted 1–4C-alkyl or —N(R11)R12,
R9 is hydrogen, 1–4C-alkyl, hydroxyl, 1–4C-alkoxy, halogen or trifluoromethyl,
R10 is hydroxyl, 1–4C-alkoxy, carboxyl, 1–4C-alkoxycarbonyl or —N(R11)R12, where
R11 is hydrogen, 1–4C-alkyl or —CO—R13 and
R12 is hydrogen or 1–4C-alkyl, or where
R11 and R12, together and including the nitrogen atom to which both are bonded, are a piperidino or morpholino radical,
R13 is hydrogen, 1–4C-alkyl or 1–4C-alkoxy,
R14 is 1–4C-alkyl and
R15 is 1–4C-alkyl, or where
R14 and R15, together and including the nitrogen atom to which both are bonded, are a piperidino or morpholino radical,
W is CH or N,
X is O (oxygen), N-1–4C-alkyl or S (sulfur),
Y is N or CH,
Z is O (oxygen), CO (carbonyl), S (sulfur) or $SO_2$,
m is a number from 2 to 5,
n is the number 0, 1 or 2,
r is a number from 0 to 5,
u is a number from 0 to 3 and
v is the number 0 or 1
and their salts,
where
R6 does not have the meaning of benzene if R5 is hydrogen or 1–4C-alkyl and v is the number 0,
r is not the number 0 if Y is N and Z is O, S or $SO_2$,
Z is not $SO_2$ if u is the number 0 and v is the number 1,
and where
R6 is not an N (nitrogen)-bonded cyclic system or bicyclic system if Z is O, S or $SO_2$, v is the number 1 and u is the number 0.

1–4C-Alkyl is straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1–4C-Alkoxy is a radical which, beside the oxygen atom, contains one of the abovementioned 1–4C-alkyl radicals. Examples which may be mentioned are the methoxy and the ethoxy radicals.

Halogen within the meaning of the present invention is bromine, chlorine and, in particular, fluorine.

1–4C-Alkylcarbonyl is a radical which, beside the carbonyl group, contains one of the abovementioned 1–4C-alkyl radicals. An example which may be mentioned is the acetyl radical.

2–4C-Alkenylcarbonyl is a radical which, beside the carbonyl group, contains a 2–4C-alkenyl radical, for example a propenyl radical or a butenyl radical. An example which may be mentioned is the acryloyl radical.

Halogen-1–4C-alkylcarbonyl is a radical which, beside the carbonyl group, contains a halogen-substituted 1–4C-alkyl radical. An example which may be mentioned is the γ-chlorobutyryl radical.

N(R14)R15-1–4C-Alkylcarbonyl is a radical which, beside the carbonyl group, contains an —N(R14)R15-substituted 1–4C-alkyl radical. An example which may be mentioned is the 3-dimethylaminopropionyl radical.

Di-1–4C-alkylcarbamoyl is a radical which, beside the carbonyl group, contains a di-1–4C-alkylamino radical. The di-1–4C-alkylamino radical is an amino radical which is substituted by two of the above-mentioned 1–4C-alkyl radicals which are identical or different. Examples which may be mentioned are the dimethylamino, the diethylamino and the diisopropylamino radicals. Di-1–4C-alkylcarbamoyl radicals which may be mentioned are, for example, the dimethylcarbamoyl and the diethylcarbamoyl radicals.

1–4C-Alkylsulfonyl is a radical which, beside the sulfonyl group (—$SO_2$—) contains one of the above-mentioned 1–4C-alkyl radicals. An example which may be mentioned is the methylsulfonyl radical.

1–4C-Alkoxycarbonyl is a radical which, beside the carbonyl group, contains one of the abovementioned 1–4C-alkoxy radicals. Examples which may be mentioned are the methoxycarbonyl and the ethoxycarbonyl radicals.

Exemplary, R4-substituted 1–4C-alkyl radicals which may be mentioned are the 2-methoxycarbonylethyl, the 2-ethoxycarbonylethyl, the methoxycarbonylmethyl, the carboxymethyl, the 2-hydroxyethyl, the methoxymethyl, the 2-methoxyethyl, the dimethylaminomethyl and the 2-dimethylaminoethyl radicals.

Cyclic systems or bicyclic systems R6 which may be mentioned, for example, are the radicals: phenyl, 2-furyl, 3-furyl, 2-thienyl, 3-thienyl, 3-pyrrolyl, 2-oxazolyl, 4-oxazolyl, 4-isoxazolyl, 5-isoxazolyl, 2-thiazolyl, 3-isothiazolyl, 2-imidazolyl, 3-pyrazolyl, 4-pyrazolyl, 1,2,3-triazol-4-yl, 1,2,5-thiadiazol-4-yl, 1,2,5-thiadiazol-4-yl-1-oxide, 1,2,4-triazol-3-yl, tetrazol-5-yl, 1,3,4-thiadiazol-2-yl, 1,2,3-thiadiazol-4-yl, 1,3,4-oxadiazol-2-yl, 2-pyridyl, 4-pyridyl, 2-pyrimidinyl, 1,3,4-triazin-2-yl, 2-benzimidazolyl, 2-imidazopyridyl, 2-benzothiazolyl and 2-benzoxazolyl.

The substituents R8 and R9 can be bonded into the cyclic systems or bicyclic systems R6 in any conceivable position. Exemplary, R8- and R9-substituted radicals R6 which may be mentioned are: 4-methylphenyl, 3-dimethylaminomethylphenyl, 3-piperidinomethylphenyl, 3-carboxymethylphenyl, 2-dimethylaminomethyl-5-methyl-3-furyl, 1-methylpyrrol-3-yl, 4,5-dimethyloxazol-2-yl, 3,5-dimethylisoxazol-4-yl, 4,5-dimethylthiazol-2-yl, 4-methyl-5-carboxymethylthiazol-2-yl, 1-methylimidazol-2-yl, 1-methylpyrazol-3-yl, 1-(2-dimethylaminoethyl)pyrazol-3-yl, 5-methyl-1,3,4-oxadiazol-2-yl, 1-methyl-1,2,3-triazol-4-yl, 1-methyl-1,2,4-triazol-3-yl, 1-(2-dimethylaminoethyl)-1,2,3-triazol-4-yl, 1-methyltetrazol-5-yl, 1-(2-dimethylaminoethyl)tetrazol-5-yl, 1-carboxymethyltetrazol-5-yl, 5-methyl-1,3,4-thiadiazol-2-yl, 5-trifluoromethyl-1,3,4-thiadiazol-2-yl, 1-(2-hydroxyethyl)tetrazol-5-yl, 2-amino-1,3,4-thiadiazol-2-yl, 3-amino-1,2,4-triazol-5-yl, 4-methyl-5-trifluoromethyl-1,2,4-triazol-3-yl, 4-aminopyrimidin-2-yl, 3-methyl-2-furyl, 2-methyl-3-furyl, 5-methyl-2-furyl, 5-ethyl-2-furyl, 3-methoxy-2-furyl, 5-dimethylaminomethyl-2-furyl, 5-N-morpholinomethyl-2-furyl, 5-methoxymethyl-2-furyl, 5-hydroxymethyl-2-furyl, 5-N-piperidinomethyl-2-furyl, 5-chloro-2-furyl, 5-fluoro-2-furyl, 5-methyl-2-thienyl, 5-chloro-2-thienyl, 3-methyl-2-thienyl, 3-amino-2-thienyl, 3-guanidino-2-thienyl, 3-methoxy-2-thienyl, 2-methyl-3-thienyl, 5-dimethylaminomethyl-2-thienyl, 5-N-morpholinomethyl-2-thienyl, 5-methyl-2-pyrrolyl, 2,5-dimethyl-1-pyrrolyl, 1,5-dimethyl-2-pyrrolyl, 1-methyl-2-pyrrolyl, 2-amino-4-thiazolyl, 2-methyl-4-thiazolyl, 2-amino-5-methyl-4-thiazolyl, 4-methyl-5-thiazolyl, 2-dimethylaminomethyl-4-thiazolyl, 2-guanidino-4-thiazolyl, 2-formylamino-4-thiazolyl, 2-N-morpholinomethyl-4-thiazolyl, 4-methyl-5-oxazolyl, 3-guanidino-1-pyrazolyl, 3-guanidino-4-pyrazolyl, 2-methyl-4-imidazolyl, 5-methyl-4-imidazolyl, 2-methyl-1-imidazolyl, 2-methyl-5-nitro-1-imidazolyl, 4,5-dimethyl-2-imidazolyl, 4-hydroxyethyl-5-methyl-1-imidazolyl, 3-methyl-1-pyrazolyl, 5-amino-1,2,4-thiadiazol-3-yl, 4-methoxy-2-pyridinyl, 4-methoxy-3-methyl-2-pyridinyl and 3,4-dimethoxypyridinyl.

Possible radicals $-C_mH_{2m}-$, $-C_rH_{2r}-$ and $-C_uH_{2u}-$ are straight-chain or branched radicals. Examples which may be mentioned are the pentylene, isopentylene (3-methylbutylene), neopentylene (2,2-dimethylpropylene), butylene, isobutylene, sec-butylene, tert-butylene, propylene, isopropylene, ethylene and (for $-C_uH_{2u}-$ and $-C_rH_{2r}-$) methylene radicals.

Radicals $-C_mH_{2m}-$ which may preferably be mentioned are the ethylene ($-CH_2CH_2-$), the butylene ($-CH_2CH_2CH_2CH_2-$) and in particular the propylene radical ($-CH_2CH_2CH_2-$). Radicals $-C_rH_{2r}-$ which may preferentially be mentioned are the ethylene, the propylene and the methylene radical. In a further preferred embodiment, r is the number 0, so that the expression $-C_rH_{2r}-$ disappears or is a bonding dash.

Radicals $-C_uH_{2u}-$ which may preferably be mentioned are the methylene, the ethylene and the propylene radicals. In a further preferred embodiment, u is the number 0, so that the expression $-C_uH_{2u}-$ disappears or is a bonding dash and the radical R6 is directly bonded to the group Z.

In a further preferred embodiment, v is the number 0, so that the expression $-Z[-C_uH_{2u}]_v-$ disappears or is a bonding dash and the radical R6 is directly bonded to the group $C_rH_{2r}$.

Suitable salts for compounds of the formula I in which n is the number 0 are all acid addition salts. Particular mention may be made of the pharmacologically tolerable salts of the inorganic and organic acids customarily used in pharmacy. Pharmacologically nontolerable salts, which can initially be obtained, for example, in the preparation of the compounds according to the invention on the industrial scale, are converted into pharmacologically tolerable salts by processes known to the person skilled in the art. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

For compounds of the formula I in which n is the number 1 and/or for compounds with a carboxyl radical, suitable salts are also salts with bases. Examples of basic salts which may be mentioned are lithium, sodium, potassium, calcium, aluminum, magnesium, titanium, ammonium, meglumine or guanidinium salts, here too the bases being employed in salt preparation in an equimolar quantitative ratio or one differing therefrom.

Compounds to be emphasized are those of the formula I (see attached formula sheet I), in which R1 is hydrogen, 1–4C-alkoxy or halogen, R2 is hydrogen or halogen, R3 is hydrogen, 1–4C-alkyl, R4-substituted 1–4C-alkyl, 1–4C-alkylcarbonyl, 2–4C-alkenylcarbonyl, halogen-1–4C-alkylcarbonyl, N(R14)R15-1–4C-alkylcarbonyl, di-1–4C-alkylcarbamoyl or 1–4C-alkylsulfonyl, R4 is —N(R14)R15, R5 is hydrogen, 1–4C-alkyl or 1–4C-alkoxy, R6 is an R8- and R9-substituted cyclic system or bicyclic system which is selected from the group consisting of benzene, furan, thiophene, thiazole, imidazole, triazole, pyridine, pyrimidine and pyridone, R7 is hydrogen or 1–4C-alkyl, R8 is hydrogen, 1–4C-alkyl, hydroxyl, 1–4C-alkoxy, halogen, nitro, guanidino, carboxyl, 1–4C-alkoxycarbonyl, R10-substituted 1–4C-alkyl or —N(R11)R12, R9 is hydrogen, 1–4C-alkyl, hydroxyl or fluorine, R10 is carboxyl, 1–4C-alkoxycarbonyl or —N(R11)R12, where R11 is 1–4C-alkyl and R12 is hydrogen or 1–4C-alkyl, or where R11 and R12, together and including the nitrogen atom to which both are bonded, are a piperidino or morpholino radical, R14 is 1–4C-alkyl and
R15 is 1–4C-alkyl, or where
R14 and R15, together and including the nitrogen atom to which both are bonded, are a piperidino or morpholino radical,
W is CH or N,
X is O (oxygen), N-1–4C-alkyl or S (sulfur),
Y is N or CH,
Z is O (oxygen), CO (carbonyl), S (sulfur) or $SO_2$,
m is a number from 2 to 4,
n is the number 0 or 1,
r is a number from 0 to 3,
u is a number from 0 to 2 and
v is the number 0 or 1
and their salts,
where
R6 does not have the meaning of benzene if R5 is hydrogen or 1–4C-alkyl and v is the number 0,
r is not the number 0 if Y is N and Z is O, S or $SO_2$,
Z is not $SO_2$ if u is the number 0 and v is the number 1, and
where
R6 is not an N (nitrogen)-bonded cyclic system or bicyclic system if Z is O, S or $SO_2$, v is the number 1 and u is the number 0.

Compounds particularly to be emphasized are those of the formula I (see attached formula sheet I), in which
R1 is hydrogen, 1–4C-alkoxy or halogen,
R2 is hydrogen or halogen,
R3 is hydrogen, R4-substituted 1–4C-alkyl, N(R14)R15-1–4C-alkylcarbonyl or 1–4C-alkylsulfonyl,
R4 is —N(R14)R15,
R5 is hydrogen, 1–4C-alkyl or 1–4C-alkoxy,
R6 is an R8- and R9-substituted cyclic system or bicyclic system which is selected from the group consisting of benzene, furan, thiophene, thiazole, imidazole, triazole, pyridine, pyrimidine and pyridone,
R7 is hydrogen,
R8 is hydrogen, 1–4C-alkyl, 1–4C-alkoxy, halogen, nitro or R10-substituted 1–4C-alkyl,
R9 is hydrogen, 1–4C-alkyl or fluorine,
R10 is —N(R11)R12, where
R11 is 1–4C-alkyl and
R12 is 1–4C-alkyl, or where
R11 and R12, together and including the nitrogen atom to which both are bonded, are a piperidino or morpholino radical,
R14 is 1–4C-alkyl and
R14 is 1–4C-alkyl, or where
R14 and R15, together and including the nitrogen atom to which both are bonded, are a piperidino or morpholino radical,
W is CH or N,
X is O (oxygen) or S (sulfur),
Y is N or CH,
Z is O (oxygen), CO (carbonyl), S (sulfur) or $SO_2$,
m is a number from 2 to 4,
n is the number 0 or 1,
r is a number from 0 to 3,
u is a number from 0 to 2 and
v is the number 0 or 1
and their salts,
where
R6 does not have the meaning of benzene if R5 is hydrogen or 1–4C-alkyl and v is the number 0,
r is not the number 0 it Y is N and Z is O, S or $SO_2$,
Z is not $SO_2$ if u is the number 0 and v is the number 1, and where
R6 is not an N (nitrogen)-bonded cyclic system or bicyclic system if Z is O, S or $SO_2$, v is the number 1 and u is the number 0.

Exemplary compounds are those of the formula I (see attached formula sheet I), in which
R1 is hydrogen,
R2 is hydrogen,
R3 is hydrogen,
R5 is 1–4C-alkyl or 1–4C-alkoxy,
R6 is an R8- and R9-substituted cyclic system or bicyclic system which is selected from the group consisting of benzene, furan, thiophene, thiazole, pyridine and pyrimidine,
R7 is hydrogen,
R8 is hydrogen, 1–4C-alkyl, halogen or R10-substituted 1–4C-alkyl,
R9 is hydrogen,
R10 is —N(R11)R12, where
R11 is 1–4C-alkyl and
R12 is 1–4C-alkyl,
W is CH,
X is S (sulfur),
Y is N or CH,
Z is CO (carbonyl) or S (sulfur),
m is the number 3,
n is the number 0,
r is a number from 0 to 3,
u is the number 0 and
v is the number 0 or 1
and their salts,
where
R6 does not have the meaning of benzene if R5 is 1–4C-alkyl and v is the number 0,
and where
r is not the number 0 if Y is N and Z is S.

One embodiment of the invention (embodiment a) are those compounds or those compounds of the formula I which are to be emphasized, particularly emphasized and which are exemplary, in which v is the number 1, Z is CO (carbonyl), r is the number 0 and u is the number 0.

A further embodiment of the invention (embodiment b) are those compounds or those compounds of the formula I which are to be emphasized, particularly emphasized and which are exemplary, in which v is the number 1, Z is S (sulfur), Y is N, r is the number 2 or 3 and u is the number 0 or 1.

A further embodiment of the invention (embodiment c) are those compounds or those compounds of the formula I which are to be emphasized, particularly emphasized and which are exemplary, in which v is the number 0 and r is a number from 0 to 3.

Exemplary compounds according to the invention are listed in the following tables;

TABLE 1

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-furyl and the following further substituent and symbol meanings:

| R1 | R5 | m | r |
|----|----|----|----|
| H | $CH_3$ | 2 | 0 |
| H | $CH_3$ | 2 | 1 |
| H | $CH_3$ | 2 | 2 |
| H | $CH_3$ | 3 | 0 |

TABLE 1-continued

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-furyl and the following further substituent and symbol meanings:

| R1 | R5 | m | r |
|---|---|---|---|
| H | CH$_3$ | 3 | 1 |
| H | CH$_3$ | 3 | 2 |
| H | CH$_3$ | 4 | 0 |
| H | CH$_3$ | 4 | 1 |
| H | CH$_3$ | 4 | 2 |
| F | CH$_3$ | 2 | 0 |
| F | CH$_3$ | 2 | 1 |
| F | CH$_3$ | 2 | 2 |
| F | CH$_3$ | 3 | 0 |
| F | CH$_3$ | 3 | 1 |
| F | CH$_3$ | 3 | 2 |
| F | CH$_3$ | 4 | 0 |
| F | CH$_3$ | 4 | 1 |
| F | CH$_3$ | 4 | 2 |
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |

TABLE 2

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 4-methyl-5-thiazolyl and the following further substituent and symbol meanings:

| R1 | R5 | m | r |
|---|---|---|---|
| H | CH$_3$ | 2 | 0 |
| H | CH$_3$ | 2 | 1 |
| H | CH$_3$ | 2 | 2 |
| H | CH$_3$ | 3 | 0 |
| H | CH$_3$ | 3 | 1 |
| H | CH$_3$ | 3 | 2 |
| H | CH$_3$ | 4 | 0 |
| H | CH$_3$ | 4 | 1 |
| H | CH$_3$ | 4 | 2 |
| F | CH$_3$ | 2 | 0 |
| F | CH$_3$ | 2 | 1 |
| F | CH$_3$ | 2 | 2 |
| F | CH$_3$ | 3 | 0 |
| F | CH$_3$ | 3 | 1 |
| F | CH$_3$ | 3 | 2 |
| F | CH$_3$ | 4 | 0 |
| F | CH$_3$ | 4 | 1 |
| F | CH$_3$ | 4 | 2 |
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |

TABLE 3

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 1-methyl-5-tetrazolyl and the following further substituent and symbol meanings:

| R1 | R5 | m | r |
|---|---|---|---|
| H | CH$_3$ | 2 | 0 |
| H | CH$_3$ | 2 | 1 |
| H | CH$_3$ | 2 | 2 |
| H | CH$_3$ | 3 | 0 |
| H | CH$_3$ | 3 | 1 |
| H | CH$_3$ | 3 | 2 |
| H | CH$_3$ | 4 | 0 |
| H | CH$_3$ | 4 | 1 |
| H | CH$_3$ | 4 | 2 |
| F | CH$_3$ | 2 | 0 |
| F | CH$_3$ | 2 | 1 |
| F | CH$_3$ | 2 | 2 |
| F | CH$_3$ | 3 | 0 |
| F | CH$_3$ | 3 | 1 |
| F | CH$_3$ | 3 | 2 |
| F | CH$_3$ | 4 | 0 |
| F | CH$_3$ | 4 | 1 |
| F | CH$_3$ | 4 | 2 |
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |

TABLE 4

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 4-pyridinyl and the following further substituent and symbol meanings:

| R1 | R5 | m | r |
|---|---|---|---|
| H | CH$_3$ | 2 | 0 |
| H | CH$_3$ | 2 | 1 |
| H | CH$_3$ | 2 | 2 |
| H | CH$_3$ | 3 | 0 |
| H | CH$_3$ | 3 | 1 |
| H | CH$_3$ | 3 | 2 |
| H | CH$_3$ | 4 | 0 |
| H | CH$_3$ | 4 | 1 |
| H | CH$_3$ | 4 | 2 |
| F | CH$_3$ | 2 | 0 |
| F | CH$_3$ | 2 | 1 |
| F | CH$_3$ | 2 | 2 |
| F | CH$_3$ | 3 | 0 |
| F | CH$_3$ | 3 | 1 |
| F | CH$_3$ | 3 | 2 |
| F | CH$_3$ | 4 | 0 |
| F | CH$_3$ | 4 | 1 |
| F | CH$_3$ | 4 | 2 |
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |

TABLE 5

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 1-imidazolyl and the following further substituent and symbol meanings:

| R1 | R5 | m | r |
|----|-----|---|---|
| H | $CH_3$ | 2 | 3 |
| H | $CH_3$ | 2 | 1 |
| H | $CH_3$ | 2 | 2 |
| H | $CH_3$ | 3 | 3 |
| H | $CH_3$ | 3 | 1 |
| H | $CH_3$ | 3 | 2 |
| H | $CH_3$ | 4 | 3 |
| H | $CH_3$ | 4 | 1 |
| H | $CH_3$ | 4 | 2 |
| F | $CH_3$ | 2 | 3 |
| F | $CH_3$ | 2 | 1 |
| F | $CH_3$ | 2 | 2 |
| F | $CH_3$ | 3 | 3 |
| F | $CH_3$ | 3 | 1 |
| F | $CH_3$ | 3 | 2 |
| F | $CH_3$ | 4 | 3 |
| F | $CH_3$ | 4 | 1 |
| F | $CH_3$ | 4 | 2 |
| H | $OCH_3$ | 2 | 3 |
| H | $OCH_3$ | 2 | 1 |
| H | $OCH_3$ | 2 | 2 |
| H | $OCH_3$ | 3 | 3 |
| H | $OCH_3$ | 3 | 1 |
| H | $OCH_3$ | 3 | 2 |
| H | $OCH_3$ | 4 | 3 |
| H | $OCH_3$ | 4 | 1 |
| H | $OCH_3$ | 4 | 2 |

TABLE 6

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 5-chloro-2-thienyl and the following further substituent and symbol meanings:

| R1 | R5 | m | r |
|----|-----|---|---|
| H | $CH_3$ | 2 | 0 |
| H | $CH_3$ | 2 | 1 |
| H | $CH_3$ | 2 | 2 |
| H | $CH_3$ | 3 | 0 |
| H | $CH_3$ | 3 | 1 |
| H | $CH_3$ | 3 | 2 |
| H | $CH_3$ | 4 | 0 |
| H | $CH_3$ | 4 | 1 |
| H | $CH_3$ | 4 | 2 |
| F | $CH_3$ | 2 | 0 |
| F | $CH_3$ | 2 | 1 |
| F | $CH_3$ | 2 | 2 |
| F | $CH_3$ | 3 | 0 |
| F | $CH_3$ | 3 | 1 |
| F | $CH_3$ | 3 | 2 |
| F | $CH_3$ | 4 | 0 |
| F | $CH_3$ | 4 | 1 |
| F | $CH_3$ | 4 | 2 |
| H | $OCH_3$ | 2 | 0 |
| H | $OCH_3$ | 2 | 1 |
| H | $OCH_3$ | 2 | 2 |
| H | $OCH_3$ | 3 | 0 |
| H | $OCH_3$ | 3 | 1 |
| H | $OCH_3$ | 3 | 2 |
| H | $OCH_3$ | 4 | 0 |
| H | $OCH_3$ | 4 | 1 |
| H | $OCH_3$ | 4 | 2 |

TABLE 7

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-methyl-5-nitro-1-imidazolyl and the following further substituent and symbol meanings:

| R1 | R5 | m | r |
|----|-----|---|---|
| H | $CH_3$ | 2 | 3 |
| H | $CH_3$ | 2 | 1 |
| H | $CH_3$ | 2 | 2 |
| H | $CH_3$ | 3 | 3 |
| H | $CH_3$ | 3 | 1 |
| H | $CH_3$ | 3 | 2 |
| H | $CH_3$ | 4 | 3 |
| H | $CH_3$ | 4 | 1 |
| H | $CH_3$ | 4 | 2 |
| F | $CH_3$ | 2 | 3 |
| F | $CH_3$ | 2 | 1 |
| F | $CH_3$ | 2 | 2 |
| F | $CH_3$ | 3 | 3 |
| F | $CH_3$ | 3 | 1 |
| F | $CH_3$ | 3 | 2 |
| F | $CH_3$ | 4 | 3 |
| F | $CH_3$ | 4 | 1 |
| F | $CH_3$ | 4 | 2 |
| H | $OCH_3$ | 2 | 3 |
| H | $OCH_3$ | 2 | 1 |
| H | $OCH_3$ | 2 | 2 |
| H | $OCH_3$ | 3 | 3 |
| H | $OCH_3$ | 3 | 1 |
| H | $OCH_3$ | 3 | 2 |
| H | $OCH_3$ | 4 | 3 |
| H | $OCH_3$ | 4 | 1 |
| H | $OCH_3$ | 4 | 2 |

TABLE 8

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-pyridine-3-carboxylic acid and the following further substituent and symbol meanings:

| R1 | R5 | m | r |
|----|-----|---|---|
| H | $CH_3$ | 2 | 0 |
| H | $CH_3$ | 2 | 1 |
| H | $CH_3$ | 2 | 2 |
| H | $CH_3$ | 3 | 0 |
| H | $CH_3$ | 3 | 1 |
| H | $CH_3$ | 3 | 2 |
| H | $CH_3$ | 4 | 0 |
| H | $CH_3$ | 4 | 1 |
| H | $CH_3$ | 4 | 2 |
| F | $CH_3$ | 2 | 0 |
| F | $CH_3$ | 2 | 1 |
| F | $CH_3$ | 2 | 2 |
| F | $CH_3$ | 3 | 0 |
| F | $CH_3$ | 3 | 1 |
| F | $CH_3$ | 3 | 2 |
| F | $CH_3$ | 4 | 0 |
| F | $CH_3$ | 4 | 1 |
| F | $CH_3$ | 4 | 2 |
| H | $OCH_3$ | 2 | 0 |
| H | $OCH_3$ | 2 | 1 |
| H | $OCH_3$ | 2 | 2 |
| H | $OCH_3$ | 3 | 0 |
| H | $OCH_3$ | 3 | 1 |
| H | $OCH_3$ | 3 | 2 |
| H | $OCH_3$ | 4 | 0 |
| H | $OCH_3$ | 4 | 1 |
| H | $OCH_3$ | 4 | 2 |

TABLE 9

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-thiazolyl and the following further substituent and symbol meanings:

| R1 | R5 | m | r |
|----|----|---|---|
| H | CH$_3$ | 2 | 0 |
| H | CH$_3$ | 2 | 1 |
| H | CH$_3$ | 2 | 2 |
| H | CH$_3$ | 3 | 0 |
| H | CH$_3$ | 3 | 1 |
| H | CH$_3$ | 3 | 2 |
| H | CH$_3$ | 4 | 0 |
| H | CH$_3$ | 4 | 1 |
| H | CH$_3$ | 4 | 2 |
| F | CH$_3$ | 2 | 0 |
| F | CH$_3$ | 2 | 1 |
| F | CH$_3$ | 2 | 2 |
| F | CH$_3$ | 3 | 0 |
| F | CH$_3$ | 3 | 1 |
| F | CH$_3$ | 3 | 2 |
| F | CH$_3$ | 4 | 0 |
| F | CH$_3$ | 4 | 1 |
| F | CH$_3$ | 4 | 2 |
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |

TABLE 10

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-imidazolyl and the following further substituent and symbol meanings:

| R1 | R5 | m | r |
|----|----|---|---|
| H | CH$_3$ | 2 | 0 |
| H | CH$_3$ | 2 | 1 |
| H | CH$_3$ | 2 | 2 |
| H | CH$_3$ | 3 | 0 |
| H | CH$_3$ | 3 | 1 |
| H | CH$_3$ | 3 | 2 |
| H | CH$_3$ | 4 | 0 |
| H | CH$_3$ | 4 | 1 |
| H | CH$_3$ | 4 | 2 |
| F | CH$_3$ | 2 | 0 |
| F | CH$_3$ | 2 | 1 |
| F | CH$_3$ | 2 | 2 |
| F | CH$_3$ | 3 | 0 |
| F | CH$_3$ | 3 | 1 |
| F | CH$_3$ | 3 | 2 |
| F | CH$_3$ | 4 | 0 |
| F | CH$_3$ | 4 | 1 |
| F | CH$_3$ | 4 | 2 |
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |

TABLE 11

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 5-nitro-1-imidazolyl and the following further substituent and symbol meanings:

| R1 | R5 | m | r |
|----|----|---|---|
| H | CH$_3$ | 2 | 3 |
| H | CH$_3$ | 2 | 1 |
| H | CH$_3$ | 2 | 2 |
| H | CH$_3$ | 3 | 3 |
| H | CH$_3$ | 3 | 1 |
| H | CH$_3$ | 3 | 2 |
| H | CH$_3$ | 4 | 3 |
| H | CH$_3$ | 4 | 1 |
| H | CH$_3$ | 4 | 2 |
| F | CH$_3$ | 2 | 3 |
| F | CH$_3$ | 2 | 1 |
| F | CH$_3$ | 2 | 2 |
| F | CH$_3$ | 3 | 3 |
| F | CH$_3$ | 3 | 1 |
| F | CH$_3$ | 3 | 2 |
| F | CH$_3$ | 4 | 3 |
| F | CH$_3$ | 4 | 1 |
| F | CH$_3$ | 4 | 2 |
| H | OCH$_3$ | 2 | 3 |
| H | OCH$_3$ | 2 | 1 |
| H | OCH$_3$ | 2 | 2 |
| H | OCH$_3$ | 3 | 3 |
| H | OCH$_3$ | 3 | 1 |
| H | OCH$_3$ | 3 | 2 |
| H | OCH$_3$ | 4 | 3 |
| H | OCH$_3$ | 4 | 1 |
| H | OCH$_3$ | 4 | 2 |

TABLE 12

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-pyridinyl and the following further substituent and symbol meanings:

| R1 | R5 | m | r |
|----|----|---|---|
| H | CH$_3$ | 2 | 0 |
| H | CH$_3$ | 2 | 1 |
| H | CH$_3$ | 2 | 2 |
| H | CH$_3$ | 3 | 0 |
| H | CH$_3$ | 3 | 1 |
| H | CH$_3$ | 3 | 2 |
| H | CH$_3$ | 4 | 0 |
| H | CH$_3$ | 4 | 1 |
| H | CH$_3$ | 4 | 2 |
| F | CH$_3$ | 2 | 0 |
| F | CH$_3$ | 2 | 1 |
| F | CH$_3$ | 2 | 2 |
| F | CH$_3$ | 3 | 0 |
| F | CH$_3$ | 3 | 1 |
| F | CH$_3$ | 3 | 2 |
| F | CH$_3$ | 4 | 0 |
| F | CH$_3$ | 4 | 1 |
| F | CH$_3$ | 4 | 2 |
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |

TABLE 13

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-pyrimidinyl and the following further substituent and symbol meanings:

| R1 | R5 | m | r |
|---|---|---|---|
| H | $CH_3$ | 2 | 0 |
| H | $CH_3$ | 2 | 1 |
| H | $CH_3$ | 2 | 2 |
| H | $CH_3$ | 3 | 0 |
| H | $CH_3$ | 3 | 1 |
| H | $CH_3$ | 3 | 2 |
| H | $CH_3$ | 4 | 0 |
| H | $CH_3$ | 4 | 1 |
| H | $CH_3$ | 4 | 2 |
| F | $CH_3$ | 2 | 0 |
| F | $CH_3$ | 2 | 1 |
| F | $CH_3$ | 2 | 2 |
| F | $CH_3$ | 3 | 0 |
| F | $CH_3$ | 3 | 1 |
| F | $CH_3$ | 3 | 2 |
| F | $CH_3$ | 4 | 0 |
| F | $CH_3$ | 4 | 1 |
| F | $CH_3$ | 4 | 2 |
| H | $OCH_3$ | 2 | 0 |
| H | $OCH_3$ | 2 | 1 |
| H | $OCH_3$ | 2 | 2 |
| H | $OCH_3$ | 3 | 0 |
| H | $OCH_3$ | 3 | 1 |
| H | $OCH_3$ | 3 | 2 |
| H | $OCH_3$ | 4 | 0 |
| H | $OCH_3$ | 4 | 1 |
| H | $OCH_3$ | 4 | 2 |

TABLE 14

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 4-methyl-3-triazolyl and the following further substituent and symbol meanings:

| R1 | R5 | m | r |
|---|---|---|---|
| H | $CH_3$ | 2 | 0 |
| H | $CH_3$ | 2 | 1 |
| H | $CH_3$ | 2 | 2 |
| H | $CH_3$ | 3 | 0 |
| H | $CH_3$ | 3 | 1 |
| H | $CH_3$ | 3 | 2 |
| H | $CH_3$ | 4 | 0 |
| H | $CH_3$ | 4 | 1 |
| H | $CH_3$ | 4 | 2 |
| F | $CH_3$ | 2 | 0 |
| F | $CH_3$ | 2 | 1 |
| F | $CH_3$ | 2 | 2 |
| F | $CH_3$ | 3 | 0 |
| F | $CH_3$ | 3 | 1 |
| F | $CH_3$ | 3 | 2 |
| F | $CH_3$ | 4 | 0 |
| F | $CH_3$ | 4 | 1 |
| F | $CH_3$ | 4 | 2 |
| H | $OCH_3$ | 2 | 0 |
| H | $OCH_3$ | 2 | 1 |
| H | $OCH_3$ | 2 | 2 |
| H | $OCH_3$ | 3 | 0 |
| H | $OCH_3$ | 3 | 1 |
| H | $OCH_3$ | 3 | 2 |
| H | $OCH_3$ | 4 | 0 |
| H | $OCH_3$ | 4 | 1 |
| H | $OCH_3$ | 4 | 2 |

TABLE 15

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 2-methyl-5-thiadiazolyl and the following further substituent and symbol meanings:

| R1 | R5 | m | r |
|---|---|---|---|
| H | $CH_3$ | 2 | 0 |
| H | $CH_3$ | 2 | 1 |
| H | $CH_3$ | 2 | 2 |
| H | $CH_3$ | 3 | 0 |
| H | $CH_3$ | 3 | 1 |
| H | $CH_3$ | 3 | 2 |
| H | $CH_3$ | 4 | 0 |
| H | $CH_3$ | 4 | 1 |
| H | $CH_3$ | 4 | 2 |
| F | $CH_3$ | 2 | 0 |
| F | $CH_3$ | 2 | 1 |
| F | $CH_3$ | 2 | 2 |
| F | $CH_3$ | 3 | 0 |
| F | $CH_3$ | 3 | 1 |
| F | $CH_3$ | 3 | 2 |
| F | $CH_3$ | 4 | 0 |
| F | $CH_3$ | 4 | 1 |
| F | $CH_3$ | 4 | 2 |
| H | $OCH_3$ | 2 | 0 |
| H | $OCH_3$ | 2 | 1 |
| H | $OCH_3$ | 2 | 2 |
| H | $OCH_3$ | 3 | 0 |
| H | $OCH_3$ | 3 | 1 |
| H | $OCH_3$ | 3 | 2 |
| H | $OCH_3$ | 4 | 0 |
| H | $OCH_3$ | 4 | 1 |
| H | $OCH_3$ | 4 | 2 |

Table 16–Table 30

Compounds of the formula I (see attached formula sheet I) as defined in Tables 1–15, but with Y=CH instead of Y=N.

TABLE 31

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = phenyl and the following further substituent and symbol meanings:

| R1 | R5 | m | r |
|---|---|---|---|
| H | $OCH_3$ | 2 | 0 |
| H | $OCH_3$ | 2 | 1 |
| H | $OCH_3$ | 2 | 2 |
| H | $OCH_3$ | 3 | 0 |
| H | $OCH_3$ | 3 | 1 |
| H | $OCH_3$ | 3 | 2 |
| H | $OCH_3$ | 4 | 0 |
| H | $OCH_3$ | 4 | 1 |
| H | $OCH_3$ | 4 | 2 |
| F | $OCH_3$ | 2 | 0 |
| F | $OCH_3$ | 2 | 1 |
| F | $OCH_3$ | 2 | 2 |
| F | $OCH_3$ | 3 | 0 |
| F | $OCH_3$ | 3 | 1 |
| F | $OCH_3$ | 3 | 2 |
| F | $OCH_3$ | 4 | 0 |
| F | $OCH_3$ | 4 | 1 |
| F | $OCH_3$ | 4 | 2 |

TABLE 32

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 4-fluorophenyl and the following further substituent and symbol meanings:

| R1 | R5 | m | r |
|---|---|---|---|
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |
| F | OCH$_3$ | 2 | 0 |
| F | OCH$_3$ | 2 | 1 |
| F | OCH$_3$ | 2 | 2 |
| F | OCH$_3$ | 3 | 0 |
| F | OCH$_3$ | 3 | 1 |
| F | OCH$_3$ | 3 | 2 |
| F | OCH$_3$ | 4 | 0 |
| F | OCH$_3$ | 4 | 1 |
| F | OCH$_3$ | 4 | 2 |

TABLE 33

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 4-methylphenyl and the following further substituent and symbol meanings:

| R1 | R5 | m | r |
|---|---|---|---|
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |
| F | OCH$_3$ | 2 | 0 |
| F | OCH$_3$ | 2 | 1 |
| F | OCH$_3$ | 2 | 2 |
| F | OCH$_3$ | 3 | 0 |
| F | OCH$_3$ | 3 | 1 |
| F | OCH$_3$ | 3 | 2 |
| F | OCH$_3$ | 4 | 0 |
| F | OCH$_3$ | 4 | 1 |
| F | OCH$_3$ | 4 | 2 |

TABLE 34

Compounds of the formula I (see attached formula sheet I) with W = CH, binding of the substituents R1 in the 5-position to benzimidazole, R2 = H, R3 = H, R7 = H, n = 0, X = S, Y = N, v = 0, R6 = 4-methylphenyl and the following further substituent and symbol meanings:

| R1 | R5 | m | r |
|---|---|---|---|
| H | OCH$_3$ | 2 | 0 |
| H | OCH$_3$ | 2 | 1 |
| H | OCH$_3$ | 2 | 2 |
| H | OCH$_3$ | 3 | 0 |
| H | OCH$_3$ | 3 | 1 |
| H | OCH$_3$ | 3 | 2 |
| H | OCH$_3$ | 4 | 0 |
| H | OCH$_3$ | 4 | 1 |
| H | OCH$_3$ | 4 | 2 |
| F | OCH$_3$ | 2 | 0 |
| F | OCH$_3$ | 2 | 1 |
| F | OCH$_3$ | 2 | 2 |
| F | OCH$_3$ | 3 | 0 |
| F | OCH$_3$ | 3 | 1 |
| F | OCH$_3$ | 3 | 2 |
| F | OCH$_3$ | 4 | 0 |
| F | OCH$_3$ | 4 | 1 |
| F | OCH$_3$ | 4 | 2 |

Tables 35–38

Compounds of the formula I (see attached formula sheet I) as defined in Tables 31–34 but with Y=CH instead of Y=N.

TABLE 39

Compounds of the formula I (see attached formula sheet I) with W = CH, R1 = H, R2 = H, R3 = H, R7 = H, n = 0, v = 1, X = S, R6 = phenyl and the following further substituent and symbol meanings:

| R5 | Y | Z | m | r | u |
|---|---|---|---|---|---|
| CH$_3$ | N | S | 2 | 2 | 0 |
| CH$_3$ | N | S | 3 | 2 | 0 |
| CH$_3$ | N | S | 4 | 2 | 0 |
| CH$_3$ | N | S | 2 | 3 | 0 |
| CH$_3$ | N | S | 3 | 3 | 0 |
| CH$_3$ | N | CO | 2 | 0 | 1 |
| CH$_3$ | N | CO | 3 | 0 | 1 |
| CH$_3$ | N | CO | 4 | 0 | 1 |
| CH$_3$ | N | CO | 2 | 1 | 0 |
| CH$_3$ | N | CO | 3 | 1 | 0 |
| CH$_3$ | CH | S | 2 | 2 | 0 |
| CH$_3$ | CH | S | 3 | 2 | 0 |
| CH$_3$ | CH | S | 4 | 2 | 0 |
| CH$_3$ | CH | S | 2 | 3 | 0 |
| CH$_3$ | CH | S | 3 | 3 | 0 |
| CH$_3$ | CH | CO | 2 | 0 | 1 |
| CH$_3$ | CH | CO | 3 | 0 | 1 |
| CH$_3$ | CH | CO | 4 | 0 | 1 |
| CH$_3$ | CH | CO | 2 | 1 | 0 |
| CH$_3$ | CH | CO | 3 | 1 | 0 |
| OCH$_3$ | N | S | 2 | 2 | 0 |
| OCH$_3$ | N | S | 3 | 2 | 0 |
| OCH$_3$ | N | S | 2 | 3 | 0 |
| OCH$_3$ | N | CO | 2 | 0 | 1 |
| OCH$_3$ | N | CO | 3 | 0 | 1 |
| OCH$_3$ | CH | S | 2 | 2 | 0 |
| OCH$_3$ | CH | S | 3 | 2 | 0 |
| OCH$_3$ | CH | S | 2 | 3 | 0 |
| OCH$_3$ | CH | CO | 2 | 0 | 1 |
| OCH$_3$ | CH | CO | 3 | 0 | 1 |

TABLE 40

Compounds of the formula I (see attached formula sheet I) with W = CH, R1 = H, R2 = H, R3 = H, R7 = H, n = 0, v = 1, X = S, R6 = 2-furyl and the following further substituent and symbol meanings:

| R5 | Y | Z | m | r | u |
|---|---|---|---|---|---|
| CH$_3$ | N | S | 2 | 2 | 0 |
| CH$_3$ | N | S | 3 | 2 | 0 |
| CH$_3$ | N | S | 4 | 2 | 0 |
| CH$_3$ | N | S | 2 | 3 | 0 |
| CH$_3$ | N | S | 3 | 3 | 0 |
| CH$_3$ | N | CO | 2 | 0 | 1 |
| CH$_3$ | N | CO | 3 | 0 | 1 |
| CH$_3$ | N | CO | 4 | 0 | 1 |
| CH$_3$ | N | CO | 2 | 1 | 0 |
| CH$_3$ | N | CO | 3 | 1 | 0 |
| CH$_3$ | CH | S | 2 | 2 | 0 |
| CH$_3$ | CH | S | 3 | 2 | 0 |
| CH$_3$ | CH | S | 4 | 2 | 0 |
| CH$_3$ | CH | S | 2 | 3 | 0 |
| CH$_3$ | CH | S | 3 | 3 | 0 |
| CH$_3$ | CH | CO | 2 | 0 | 1 |
| CH$_3$ | CH | CO | 3 | 0 | 1 |
| CH$_3$ | CH | CO | 4 | 0 | 1 |
| CH$_3$ | CH | CO | 2 | 1 | 0 |
| CH$_3$ | CH | CO | 3 | 1 | 0 |
| OCH$_3$ | N | S | 2 | 2 | 0 |
| OCH$_3$ | N | S | 3 | 2 | 0 |
| OCH$_3$ | N | S | 2 | 3 | 0 |
| OCH$_3$ | N | CO | 2 | 0 | 1 |
| OCH$_3$ | N | CO | 3 | 0 | 1 |
| OCH$_3$ | CH | S | 2 | 2 | 0 |
| OCH$_3$ | CH | S | 3 | 2 | 0 |
| OCH$_3$ | CH | S | 2 | 3 | 0 |
| OCH$_3$ | CH | CO | 2 | 0 | 1 |
| OCH$_3$ | CH | CO | 3 | 0 | 1 |

TABLE 41

Compounds of the formula I (see attached formula sheet I) with W = CH, R1 = H, R2 = H, R3 = H, R7 = H, n = 0, v = 1, X = S, R6 = 4-fluorophenyl and the following further substituents and symbol meanings:

| R5 | Y | Z | m | r | u |
|---|---|---|---|---|---|
| CH$_3$ | N | S | 2 | 2 | 0 |
| CH$_3$ | N | S | 3 | 2 | 0 |
| CH$_3$ | N | S | 4 | 2 | 0 |
| CH$_3$ | N | S | 2 | 3 | 0 |
| CH$_3$ | N | S | 3 | 3 | 0 |
| CH$_3$ | N | CO | 2 | 0 | 1 |
| CH$_3$ | N | CO | 3 | 0 | 1 |
| CH$_3$ | N | CO | 4 | 0 | 1 |
| CH$_3$ | N | CO | 2 | 1 | 0 |
| CH$_3$ | N | CO | 3 | 1 | 0 |
| CH$_3$ | CH | S | 2 | 2 | 0 |
| CH$_3$ | CH | S | 3 | 2 | 0 |
| CH$_3$ | CH | S | 4 | 2 | 0 |
| CH$_3$ | CH | S | 2 | 3 | 0 |
| CH$_3$ | CH | S | 3 | 3 | 0 |
| CH$_3$ | CH | CO | 2 | 0 | 1 |
| CH$_3$ | CH | CO | 3 | 0 | 1 |
| CH$_3$ | CH | CO | 4 | 0 | 1 |
| CH$_3$ | CH | CO | 2 | 1 | 0 |
| CH$_3$ | CH | CO | 3 | 1 | 0 |
| OCH$_3$ | N | S | 2 | 2 | 0 |
| OCH$_3$ | N | S | 3 | 2 | 0 |
| OCH$_3$ | N | S | 2 | 3 | 0 |
| OCH$_3$ | N | CO | 2 | 0 | 1 |
| OCH$_3$ | N | CO | 3 | 0 | 1 |
| OCH$_3$ | CH | S | 2 | 2 | 0 |
| OCH$_3$ | CH | S | 3 | 2 | 0 |
| OCH$_3$ | CH | S | 2 | 3 | 0 |
| OCH$_3$ | CH | CO | 2 | 0 | 1 |
| OCH$_3$ | CH | CO | 3 | 0 | 1 |

TABLE 42

Compound of the formula I (see attached formula sheet I) with W = CH, R1 = H, R2 = H, R3 = H, R7 = H, n = 0, v = 1, X = S, R6 = 5-chloro-2-thienyl and the following further substituent and symbol meanings:

| R5 | Y | Z | m | r | u |
|---|---|---|---|---|---|
| CH$_3$ | N | S | 2 | 2 | 0 |
| CH$_3$ | N | S | 3 | 2 | 0 |
| CH$_3$ | N | S | 4 | 2 | 0 |
| CH$_3$ | N | S | 2 | 3 | 0 |
| CH$_3$ | N | S | 3 | 3 | 0 |
| CH$_3$ | N | CO | 2 | 0 | 1 |
| CH$_3$ | N | CO | 0 | - | 1 |
| CH$_3$ | N | CO | 4 | 0 | 1 |
| CH$_3$ | N | CO | 2 | 1 | 0 |
| CH$_3$ | N | CO | 3 | 1 | 0 |
| CH$_3$ | CH | S | 2 | 2 | 0 |
| CH$_3$ | CH | S | 3 | 2 | 0 |
| CH$_3$ | CH | S | 4 | 2 | 0 |
| CH$_3$ | CH | S | 2 | 3 | 0 |
| CH$_3$ | CH | S | 3 | 3 | 0 |
| CH$_3$ | CH | CO | 2 | 0 | 1 |
| CH$_3$ | CH | CO | 3 | 0 | 1 |
| CH$_3$ | CH | CO | 4 | 0 | 1 |
| CH$_3$ | CH | CO | 2 | 1 | 0 |
| CH$_3$ | CH | CO | 3 | 1 | 0 |
| OCH$_3$ | N | S | 2 | 2 | 0 |
| OCH$_3$ | N | S | 3 | 2 | 0 |
| OCH$_3$ | N | S | 2 | 3 | 0 |
| OCH$_3$ | N | CO | 2 | 0 | 1 |
| OCH$_3$ | N | CO | 3 | 0 | 1 |
| OCH$_3$ | CH | S | 2 | 2 | 0 |
| OCH$_3$ | CH | S | 3 | 2 | 0 |
| OCH$_3$ | CH | S | 2 | 3 | 0 |
| OCH$_3$ | CH | CO | 2 | 0 | 1 |
| OCH$_3$ | CH | CO | 3 | 0 | 1 |

TABLE 43

Compound of the formula I (see attached formula sheet 1) with W = CH, R1 = H, R2 = H, R3 = H, R7 = H, n = 0, v = 1, X = S, R6 = 2-methyl-5-nitro-1-imidazolyl and the following further substituent and symbol meanings:

| R5 | Y | Z | m | r | u |
|---|---|---|---|---|---|
| CH$_3$ | N | S | 2 | 2 | 2 |
| CH$_3$ | N | S | 3 | 2 | 2 |
| CH$_3$ | N | S | 4 | 2 | 2 |
| CH$_3$ | N | S | 2 | 3 | 2 |
| CH$_3$ | N | S | 3 | 3 | 2 |
| CH$_3$ | N | CO | 2 | 0 | 2 |
| CH$_3$ | N | CO | 3 | 0 | 2 |
| CH$_3$ | N | CO | 4 | 0 | 2 |
| CH$_3$ | N | CO | 2 | 1 | 2 |
| CH$_3$ | N | CO | 3 | 1 | 2 |
| CH$_3$ | CH | S | 2 | 2 | 2 |
| CH$_3$ | CH | S | 3 | 2 | 2 |
| CH$_3$ | CH | S | 4 | 2 | 2 |

TABLE 43-continued

Compound of the formula I (see attached formula sheet 1) with W = CH, R1 = H, R2 = H, R3 = H, R7 = H, n = 0, v = 1, X = S, R6 = 2-methyl-5-nitro-1-imidazolyl and the following further substituent and symbol meanings:

| R5 | Y | Z | m | r | u |
|---|---|---|---|---|---|
| CH$_3$ | CH | S | 2 | 3 | 2 |
| CH$_3$ | CH | S | 3 | 3 | 2 |
| CH$_3$ | CH | CO | 2 | 0 | 2 |
| CH$_3$ | CH | CO | 3 | 0 | 2 |
| CH$_3$ | CH | CO | 4 | 0 | 2 |
| CH$_3$ | CH | CO | 3 | 1 | 2 |
| CH$_3$ | CH | CO | 3 | 1 | 2 |
| OCH$_3$ | N | S | 2 | 2 | 2 |
| OCH$_3$ | N | S | 3 | 2 | 2 |
| OCH$_3$ | N | S | 2 | 3 | 2 |
| OCH$_3$ | N | CO | 2 | 0 | 2 |
| OCH$_3$ | N | CO | 3 | 0 | 2 |
| OCH$_3$ | CH | S | 2 | 2 | 2 |
| OCH$_3$ | CH | S | 3 | 2 | 2 |
| OCH$_3$ | CH | S | 2 | 3 | 2 |
| OCH$_3$ | CH | CO | 2 | 0 | 2 |
| OCH$_3$ | CH | CO | 3 | 0 | 2 |

TABLE 44

Compound of the formula I (see attached formula sheet I) with W = CH, R1 = H, R2 = H, R3 = H, R7 = H, n = 0, v = 1, X = S, R6 = 2-pyridinyl and the following further substituent and symbol meanings:

| R5 | Y | Z | m | r | u |
|---|---|---|---|---|---|
| CH$_3$ | N | S | 2 | 2 | 0 |
| CH$_3$ | N | S | 3 | 2 | 0 |
| CH$_3$ | N | S | 4 | 2 | 0 |
| CH$_3$ | N | S | 2 | 3 | 0 |
| CH$_3$ | N | S | 3 | 3 | 0 |
| CH$_3$ | N | CO | 2 | 0 | 1 |
| CH$_3$ | N | CO | 3 | 0 | 1 |
| CH$_3$ | N | CO | 4 | 0 | 1 |
| CH$_3$ | N | CO | 2 | 1 | 0 |
| CH$_3$ | N | CO | 3 | 1 | 0 |
| CH$_3$ | CH | S | 2 | 2 | 0 |
| CH$_3$ | CH | S | 3 | 2 | 0 |
| CH$_3$ | CH | S | 4 | 2 | 0 |
| CH$_3$ | CH | S | 2 | 3 | 0 |
| CH$_3$ | CH | S | 3 | 3 | 0 |
| CH$_3$ | CH | CO | 2 | 0 | 1 |
| CH$_3$ | CH | CO | 3 | 0 | 1 |
| CH$_3$ | CH | CO | 4 | 0 | 1 |
| CH$_3$ | CH | CO | 2 | 1 | 0 |
| CH$_3$ | CH | CO | 3 | 1 | 0 |
| OCH$_3$ | N | S | 2 | 2 | 0 |
| OCH$_3$ | N | S | 3 | 2 | 0 |
| OCH$_3$ | N | S | 2 | 3 | 0 |
| OCH$_3$ | N | CO | 2 | 0 | 1 |
| OCH$_3$ | N | CO | 3 | 0 | 1 |
| OCH$_3$ | CH | S | 2 | 2 | 0 |
| OCH$_3$ | CH | S | 3 | 2 | 0 |
| OCH$_3$ | CH | S | 2 | 3 | 0 |
| OCH$_3$ | CH | CO | 2 | 0 | 1 |
| OCH$_3$ | CH | CO | 3 | 0 | 1 |

TABLE 45

Compound of the formula I (see attached formula sheet I) with W = CH, R1 = H, R2 = H, R3 = H, R7 = H, n = 0, v = 1, X = S, R6 = 1-methyl-5-tetrazolyl and the following further substituent and symbol meaning.

| R5 | Y | Z | m | r | u |
|---|---|---|---|---|---|
| CH$_3$ | N | S | 2 | 2 | 0 |
| CH$_3$ | N | S | 3 | 2 | 0 |
| CH$_3$ | N | S | 4 | 2 | 0 |
| CH$_3$ | N | S | 2 | 3 | 0 |
| CH$_3$ | N | S | 3 | 3 | 0 |
| CH$_3$ | N | CO | 2 | 0 | 1 |
| CH$_3$ | N | CO | 3 | 0 | 1 |
| CH$_3$ | N | CO | 4 | 0 | 1 |
| CH$_3$ | N | CO | 2 | 1 | 0 |
| CH$_3$ | N | CO | 3 | 1 | 0 |
| CH$_3$ | CH | S | 2 | 2 | 0 |
| CH$_3$ | CH | S | 3 | 2 | 0 |
| CH$_3$ | CH | S | 4 | 2 | 0 |
| CH$_3$ | CH | S | 2 | 3 | 0 |
| CH$_3$ | CH | S | 3 | 3 | 0 |
| CH$_3$ | CH | CO | 2 | 0 | 1 |
| CH$_3$ | CH | CO | 3 | 0 | 1 |
| CH$_3$ | CH | CO | 4 | 0 | 1 |
| CH$_3$ | CH | CO | 2 | 1 | 0 |
| CH$_3$ | CH | CO | 3 | 1 | 0 |
| OCH$_3$ | N | S | 2 | 2 | 0 |
| OCH$_3$ | N | S | 3 | 2 | 0 |
| OCH$_3$ | N | S | 2 | 3 | 0 |
| OCH$_3$ | N | CO | 2 | 0 | 1 |
| OCH$_3$ | N | CO | 3 | 0 | 1 |
| OCH$_3$ | CH | S | 2 | 2 | 0 |
| OCH$_3$ | CH | S | 3 | 2 | 0 |
| OCH$_3$ | CH | S | 2 | 3 | 0 |
| OCH$_3$ | CH | CO | 2 | 0 | 1 |
| OCH$_3$ | CH | CO | 3 | 0 | 1 |

TABLE 46

Compounds of the formula 1 (see attached formula sheet I) with W = CH, R1 = H, R2 = H, R3 = H, R7 = H, n = 0, v = 1, X = S, R6 = 4-pyridinyl and the following further substituent and symbol meanings:

| R5 | Y | Z | m | r | u |
|---|---|---|---|---|---|
| CH$_3$ | N | S | 2 | 2 | 0 |
| CH$_3$ | N | S | 3 | 2 | 0 |
| CH$_3$ | N | S | 4 | 2 | 0 |
| CH$_3$ | N | S | 2 | 3 | 0 |
| CH$_3$ | N | S | 3 | 3 | 0 |
| CH$_3$ | N | CO | 2 | 0 | 1 |
| CH$_3$ | N | CO | 3 | 0 | 1 |
| CH$_3$ | N | CO | 4 | 0 | 1 |
| CH$_3$ | N | CO | 2 | 1 | 0 |
| CH$_3$ | N | CO | 3 | 1 | 0 |
| CH$_3$ | CH | S | 2 | 2 | 0 |
| CH$_3$ | CH | S | 3 | 2 | 0 |
| CH$_3$ | CH | S | 4 | 2 | 0 |
| CH$_3$ | CH | S | 2 | 3 | 0 |
| CH$_3$ | CH | S | 3 | 3 | 0 |
| CH$_3$ | CH | CO | 2 | 0 | 1 |
| CH$_3$ | CH | CO | 3 | 0 | 1 |
| CH$_3$ | CH | CO | 4 | 0 | 1 |
| CH$_3$ | CH | CO | 2 | 1 | 0 |
| CH$_3$ | CH | CO | 3 | 1 | 0 |
| OCH$_3$ | N | S | 2 | 2 | 0 |
| OCH$_3$ | N | S | 3 | 2 | 0 |
| OCH$_3$ | N | S | 2 | 3 | 0 |
| OCH$_3$ | N | CO | 2 | 0 | 1 |
| OCH$_3$ | N | CO | 3 | 0 | 1 |
| OCH$_3$ | CH | S | 2 | 2 | 0 |

TABLE 46-continued

Compounds of the formula 1 (see attached formula sheet I) with W = CH, R1 = H, R2 = H, R3 = H, R7 = H, n = 0, v = 1, X = S, R6 = 4-pyridinyl and the following further substituent and symbol meanings:

| R5 | Y | Z | m | r | u |
|---|---|---|---|---|---|
| OCH$_3$ | CH | S | 3 | 2 | 0 |
| OCH$_3$ | CH | S | 2 | 3 | 0 |
| OCH$_3$ | CH | CO | 2 | 0 | 1 |
| OCH$_3$ | CH | CO | 3 | 0 | 1 |

TABLE 47

Compounds of the formula I (see attached formula sheet I) with W = CH, R1 = H, R2 = H, R3 = H, R7 = H, n = 0, v = 1, X = S, R6 = 5-nitro-1-imidazolyl and the following further substituent and symbol meanings:

| R5 | Y | Z | m | r | u |
|---|---|---|---|---|---|
| CH$_3$ | N | S | 2 | 2 | 2 |
| CH$_3$ | N | S | 3 | 2 | 2 |
| CH$_3$ | N | S | 4 | 2 | 2 |
| CH$_3$ | N | S | 2 | 3 | 2 |
| CH$_3$ | N | S | 3 | 3 | 2 |
| CH$_3$ | N | CO | 2 | 0 | 2 |
| CH$_3$ | N | CO | 3 | 0 | 2 |
| CH$_3$ | N | CO | 4 | 0 | 2 |
| CH$_3$ | N | CO | 2 | 1 | 2 |
| CH$_3$ | N | CO | 3 | 1 | 2 |
| CH$_3$ | CH | S | 2 | 2 | 2 |
| CH$_3$ | CH | S | 3 | 2 | 2 |
| CH$_3$ | CH | S | 4 | 2 | 2 |
| CH$_3$ | CH | S | 2 | 3 | 2 |
| CH$_3$ | CH | S | 3 | 3 | 2 |
| CH$_3$ | CH | CO | 2 | 0 | 2 |
| CH$_3$ | CH | CO | 3 | 0 | 2 |
| CH$_3$ | CH | CO | 4 | 0 | 2 |
| CH$_3$ | CH | CO | 2 | 1 | 2 |
| CH$_3$ | CH | CO | 3 | 1 | 2 |
| OCH$_3$ | N | S | 2 | 2 | 2 |
| OCH$_3$ | N | S | 3 | 2 | 2 |
| OCH$_3$ | N | S | 2 | 3 | 2 |
| OCH$_3$ | N | CO | 2 | 0 | 2 |
| OCH$_3$ | N | CO | 3 | 0 | 2 |
| OCH$_3$ | CH | S | 2 | 2 | 2 |
| OCH$_3$ | CH | S | 3 | 2 | 2 |
| OCH$_3$ | CH | S | 2 | 3 | 2 |
| OCH$_3$ | CH | CO | 2 | 0 | 2 |
| OCH$_3$ | CH | CO | 3 | 0 | 2 | and the salts of the compounds listed in the above tables.

The invention further relates to a process for the preparation of the compounds of the formula I and their salts.

The process comprises a) reacting mercaptobenzimidazoles of the formula II (see attached formula sheet II), in which a, R1, R2 and R3 have the meanings indicated above, with picoline derivatives III (see attached formula sheet II), in which R5, R6, R7, X, Y, Z, m, r, u and v have the meanings indicated above and A is a suitable leaving group, or b) reacting compounds of the formula IV (see attached formula sheet II), in which W, R1, R2, R3, R5, R7, X and m have the meanings indicated above, n is the number 0 and A is a suitable leaving group, with compounds of the formula V (see attached formula sheet II), in which R6, Y, Z, r, u and v have the meanings indicated above, or c) reacting compounds of the formula VI (see attached formula sheet III), in which W, R1, R2, R3, R5, R7 and n have the meanings indicated above and Hal is a halogen atom, with compounds VII (see attached formula sheet III) in which R6, X, Y, Z, m, r, u and v have the meanings indicated above, or d) reacting benzimidazoles of the formula VIII (see attached formula sheet III), in which R1, R2, R3 and W have the meanings indicated above and A is a suitable leaving group, with pyridines of the formula IX (see attached formula sheet III), in which R5, R6, R7, X, Y, Z, m, r, u and v have the meanings indicated above, and (if compounds of the formula I with n=1 or 2 and/or Z=SO$_2$ are the desired final products), then oxidizing the compounds obtained, with n=0 and/or Z=S and/or if desired then converting compounds obtained into the salts and/or if desired then converting salts obtained into the free compounds.

In the reactions mentioned above, the starting compounds can be employed as such or optionally in the form of their salts.

Suitable leaving groups A which may be mentioned are, for example, halogen atoms, in particular chlorine, or hydroxyl groups activated by esterification (e.g. with p-toluenesulfonic acid).

The reaction of II with III is carried out in suitable, preferably polar, protic or aprotic solvents (such as methanol, ethanol, isopropanol, dimethyl sulfoxide, acetone, dimethylformamide or acetonitrile) with addition or with exclusion of water. It is carried out, for example, in the presence of a proton acceptor. Those which are suitable are alkali metal hydroxides, such as sodium hydroxide, alkali metal carbonates, such as potassium carbonate, or tertiary amines, such as pyridine, triethylamine or ethyldiisopropylamine. Alternatively, the reaction can also be carried out without proton acceptors, it optionally first being possible—depending on the nature of the starting compounds—to separate off the acid addition salts in particularly pure form. The reaction temperature can be between 0° and 150° C., in the presence of proton acceptors at temperatures between 20° and 80° C. and without proton acceptors between 60° and 120°—in particular the boiling temperature of the solvents used—being preferred. The reaction times are between 0.5 and 30 hours.

The reaction of the compounds IV with the compounds V is carried out in a similar manner to the reaction of the compounds II with the compounds III, if desired with addition of catalytic amounts of alkali metal iodide, e.g. sodium iodide.

The reaction of the compounds VI with the compounds VII is carried out in a manner known per se, such as is known to the person skilled in the art for the preparation of sulfides from thiols and halogenated aromatics. The halogen atom Hal is preferably a chlorine atom.

In principle, the reaction of the compounds VIII with the compounds IX is carried out in an analogous manner to the reaction of the compounds II with the compounds III.

The oxidation of the sulfides to the sulfoxides or sulfones is carried out under the conditions which are familiar to the person skilled in the art for the oxidation of sulfides to sulfoxides or sulfones [see for this, for example, J. Drabowicz and M. Mikolajczyk, Organic Preparations and Procedures Int. 14(1–2), 45–89(1982) or E. Block in S. Patai, The Chemistry of Functional Groups, Supplement E. Part 1, p. 539–608, John Wiley and Sons (Interscience Publication), 1980]. Possible oxidants are all reagents customarily used for the oxidation of sulfides to sulfoxides or sulfones, in particular peroxy acids, such as, for example, peroxyacetic acid, trifluoroperoxyacetic acid, 3,5-dinitroperoxybenzoic acid, peroxymaleic acid, magnesium monoperoxyphthalate or preferably m-chloroperoxybenzoic acid.

The reaction temperature (depending on the reactivity of the oxidant and degree of dilution) is between −70° C. and the boiling temperature of the solvent used, but preferably between −30° and +20° C. Oxidation with halogens or with hypohalites (e.g. aqueous sodium hypochlorite solution), which is expediently carried out at temperatures between 0° and 50° C., has also proven to be advantageous. The reaction is expediently carried out in inert solvents, e.g. aromatic or chlorinated hydrocarbons, such as benzene, toluene, dichloromethane or chloroform, preferably in esters or ethers, such as ethyl acetate, isopropyl acetate or dioxane, or in alcohols, preferably isopropanol.

The sulfoxides according to the invention are optically active compounds. Depending on the nature of the substituents, there can additionally be further chiral centers in the molecule. The invention therefore comprises both the enantiomers and diastereomers and their mixtures and racemates. The enantiomers can be separated (see, for example, WO92/08716) in a manner known per se (for example by preparation and separation of appropriate diastereoisomeric compounds).

Depending on the nature of the substituents R6, the sulfones ($Z=SO_2$) are also obtained in the oxidation to give the sulfoxides n=1. Otherwise, the respective sulfides and sulfoxides or sulfones can be prepared by choice of suitable starting compounds or by use of selective oxidants.

The compounds II are disclosed, for example, in WO86/02646, EP 134 400, EP 127 763 or WO93/24480. The compounds III can, for example, be prepared analogously thereto, as described in the following examples.

The starting compounds needed for the preparation of III can, for example, be prepared from the corresponding halogen compounds analogously to J. Med. Chem. 14 (1971) 349.

The compounds IV, V, VI, VII, VIII and IX are also known or can be prepared in an analogous manner from known starting compounds by processes known per se. Thus, for example, compounds of the formula VI are obtained by reaction of compounds of the formula II with 4-halopyridines corresponding to compounds of the formula III. The compounds IV are obtained, for example (as also described in greater detail in the following examples), by reaction of compounds of the formula II with 4-(ω-haloalkylthio)pyridines corresponding to compounds of the formula III.

The following examples illustrate the invention in greater detail without restricting it. The compounds according to the invention and thee starting compounds can be prepared in an analogous manner to that described in the examples. The abbreviation RT stands for room temperature, h stands for hour(s), m.p. for melting point and dec. for decomposition.

EXAMPLES 1. 2-{[3-Methyl-4-[3-[4(2-pyrimidinyl)piperazin-1-yl] propylthio-2-pyridinyl]methyl]thio}-1H-benzimidazole 2-{[[4-(3-Chloropropylthio)-3-methyl-2-pyridinyl] methyl]thio}-1H-benzimidazole (3 mmol) is stirred at 100° C. for 36 h in acetonitrile (20 ml) with N-(2-pyrimidinyl) piperazine (3.1 mmol), potassium carbonate (15 mmol) and sodium iodide (0.3 mmol). The inorganic salts are filtered, the filtrate is concentrated and the residue is crystallized by addition of water. The title compound is obtained; beige powder; m.p. 100–103° C.; yield 81% of theory.

2. 2-{[3Methyl-4-[3-[4-(2-pyridinyl)piperazin-1-yl] propylthio-2-pyridinyl]methyl]thio}-1H-benzimidazole According to the procedure indicated in Example 1), reaction with N-(2-pyridinyl)piperazine gives the title compound; m.p. 79–82° C.; yield 75% of theory.

3. 2-{[[4-[3-[4-(5-chlorothiophen-2-yl-methyl)piperazin-1-yl]propylthio]-3-methyl-2-pyridinyl]methyl]thio}-1H-benzimidazole According to the procedure indicated in Example 1), N-(5-chlorothiophen-1-ylmethyl)piperazine gives, after chromatography on silica gal (ethyl acetate/methanol/ ammonia) and subsequent crystallization from dichloromethane/diisopropyl ether, the title compound; m.p. 125° C. (decomposition); yield 84%.

4. 2-{[3-Methyl-4-[3-[4-(2-pyridinylthiopropyl) piperazin-1-yl]-propylthio-2-pyridinyl]methyl]thio}-1H-benzimidazole According to the procedure indicated in Examples 1) and 3), N-(2-pyridinylthiopropyl)piperazine gives the title compound; m.p. 116–118° C.; yield 29%.

5. 2-{[[4-(3-[4-(4-Fluorobenzoyl)piperidin-1-yl]-propylthio]-3-methyl-2-pyridinyl]methyl]thio}-1H-benzimidazole According to the procedure indicated in Examples 1) and 3), 4-(4-fluorobenzoyl)piperidine gives the title compound; m.p. 126–129° C.; yield 44%.

6. 2-{[[4-[3-(4-Benzoylpiperidin-1-yl)-propylthio]-3-methyl-2-pyridinyl]methyl]thio}-1H-benzimidazole trihydrochloride According to the procedure indicated in Examples 1) and 3), 4-benzoylpiperidine, after conversion into the hydrochloride with conc. hydrochloric acid in isopropanol, gives the title compound; m.p. 180–182° C., dec.; yield 63%.

7. 2-{[[4-[3-[4-(5-Dimethylaminomethylfuran-2-yl-methyl) piperazin-1-yl]-propylthio]-3-methyl-2-pyridinyl] methyl]thio}-1H-benzimidazole pentahydrochloride According to the procedure indicated in Examples 1), 3) and 6), N-(5-dimethylaminomethylfuran-2-yl-methyl) piperazine gives the title compound; m.p. 150° C., dec.; yield 63%, colorless crystals.

8. 2-{[[3-Methyl-4-[3-[4-[(4-methylthiazol-5-yl)-2-ethyl] piperazin-1-yl]propylthiol-2-pyridinyl]-methyl]thio}-1H-benzimidazole trihydrochloride According to the procedure indicated in Examples 1), 3) and 6), N-[(4-methylthiazol-5-yl)-2-ethyl]-piperazine gives the title compound, m.p. 120° C., dec.; yield 57%.

9. 2-{[[4-[3-(4-Benzylpiperazin-1-yl)propylthio]-3-methoxy-2-pyridinyl]-methyl]thio}-1H-benzimidazole trihydrochloride According to the procedure indicated in Examples 1), 3) and 6), reaction of 2-{[[4-(3-chloropropylthio)-3-methoxy-2-pyridinyl]methyl]thio}-1H-benzimidazole with N-benzylpiperazine and subsequent conversion into the hydrochloride gives the title compound; m.p. 180° C., dec.; colorless crystals; yield 59% of theory.

10. 2-{[[4-[3-(4-Benzylpiperidin-1-yl)propylthio]-3-methoxy-2-pyridinyl]methyl]thio}-1H-benzimidazole According to the procedure indicated in Example 1), reaction of 2-{[[4-(3-chloropropylthio)-3-methoxy-2-pyridinyl]methyl]thio}-1H-benzimidazole with N-benzylpiperidine gives the title compound; beige powder; m.p. 73–75° C. (hydrated).

11. 2-{[[4-[3-(4-Phenylpiperazin-1-yl)propylthio]-3-methoxy-2-pyridinyl]-methyl]thio}-1H-benzimidazole trihydrochloride According to the procedure indicated in Examples 1), 3) and 6), reaction of 2-{[[4-(3-chloropropylthio)-3-methoxy-2-pyridinyl]methyl]thio}-1H-benzimidazole with N-phenylpiperazine and subsequent conversion into the hydrochloride in acetone gives the title compound; colorless crystals; m.p. 105° C., dec.; yield 73%.

12. 2-{[[4-[3-[4-(5-Chlorothiophen-2-yl-methyl)-piperazin-1-yl]propylthio]-3-methyl-2-pyridinyl]methyl]sulfinyl}-1H-benzimidazole 0.7 g (1.28 mmol) of 2-{[[4-[3-[4-(5-chlorothiophen-2-ylmethyl)piperazin-1-yl]propylthio-3-methyl-2-pyridinyl]

methyl]thio}-1H-benzimidazole is dissolved in a mixture of 15 ml of dioxane and 2.57 ml (5.14 mmol) of 2 M NaOH. 1.63 ml (3.2 mmol) of 12% strength sodium hypochlorite solution are slowly added dropwise during the course of 30 min. 2 ml of 1 M sodium thiosulfate solution are then added. The mixture is stirred at RT for 10 min. The dioxane is stripped off. The residue is neutralized with sodium dihydrogen-phosphate solution and extracted three times with dichloromethane. The combined organic phases are dried over magnesium sulfate, filtered and concentrated. The residue is chromatographed on silica gel using ethyl acetate/methanol/conc. ammonia=8.5/1/0.5. The title compound crystallizes on concentration. Yield 0.3 g (42% of theory), m.p. 54–58° C.

13. 2-{[[4-[3-(4-Benzylpiperazin-1-yl)propylthio]-3-methyl-2-pyridinyl]methyl]thio}-5-fluoro-1H-benzimidazole dihydrochloride According to the procedure indicated in Example 1), reaction of 2-{[[4-(3-chloropropylthio)-3-methyl-2-pyridinyl]methyl]thio}-5-fluoro-1H-benzimidazole with N-benzylpiperazine gives the title compound as a beige powder. Yield 80%, m.p. 130–133° C.

14. 2-{[[4-[3-[4-(5-Chlorothiophen-2-ylmethyl)-piperazin-1-yl]propylthio]-3-methyl-2-pyridinyl]-methyl]thio}-5-fluoro-1H-benzimidazole According to the procedure indicated in Example 1), reaction of 2-{[[4-(3-chloropropylthio)-3-methyl-2-pyridinyl]methylthio)-5-fluoro-1H-benzimidazole with N-(5-chlorothiophen-1-ylmethyl)piperazine gives, after chromatography on silica gel (ethyl acetate/methanol/ammonia=19:1:0.1) and subsequent crystlalization from diisopropyl ether, the title compound as a beige powder; yield 20%, m.p. 116–119° C.

15. 2-{[[4-[3-[4-(5-Chlorothiophen-2-ylmethyl)-piperazin-1-yl]propylthio]-3-methyl-2-pyridinyl]-methyl]thio}-5,6-difluoro-1H-benzimidazole According to the procedure indicated in Example 1), reaction of 2-{[[4-(3-chloropropylthio)-3-methyl-2-pyridinyl]methyl]thio}-5,6-difluoro-1H-benzimidazole with N-(5-chlorothiophen-1-ylmethyl)piperazine and subsequent crystallization from ethyl acetate gives the title compound as a beige powder; yield 50%, m.p. 79–82° C.

16. 2-{[[4-[3-[4-(5-Chlorothiophen-2-ylmethyl)-piperazin-1-yl]propylthio]-3-methyl-2-pyridinyl]-methyl]thio}-5-fluoro-6-methoxy-1H-benzimidazole difumarate According to the procedure indicated in Example 1), reaction of 2-{[[4-(3-chloropropylthio)-3-methyl-2-pyridinyl]methylthio}-5-fluoro-6-methoxy-1H-benzimidazole with N-(5-chlorothiophen-1-ylmethyl)-piperazine gives, after extraction with ethyl acetate, concentration of the organic extracts and subsequent crystallization with 2 equivalents of fumaric acid from hot acetone, the title compound as a beige powder; yield 45%, m.p. 141–146° C.

Starting compounds

A1. 2-{[[4-(3-Chloropropylthio)-3-methyl-2-pyridinyl]-methyl]thio}-1H-benzimidazole One equivalent of 2-chloromethyl-4-(3-chloropropylthio)-3-methylpyridine hydrochloride (dissolved in 10 ml of water) is added dropwise at 40° C. in the course of 20 min. to a solution of 2-mercapto-1H-benzimidazole (1.5 g/10 mmol) in 40 ml of ethanol and 21 ml of 1 N sodium hydroxide solution. The mixture is then stirred for 2–3 h at 50–60° C. and a further 3–4 h at room temperature, ethanol is distilled off on a rotary evaporator (1 kPa/40° C.), the residue is extracted 3 times with 20 ml of dichloromethane each time, and the extracts are washed with 0.1 N sodium hydroxide solution, dried over potassium carbonate and concentrated completely in vacuo. For purification, the crude product is chromatographed on silica gel (dichloromethane/methanol 20:1); the collected pure fractions are jointly concentrated in vacuo and the residue is crystallized from dichloromethane/diisopropyl ether. It is then recrystallized from methanol/toluene. Yield 2.67 g (74%) of the title compound as a colorless solid of m.p. 112–114° C.

A2. 2-Chloromethyl-4-(3-chloropropylthio)-3-methylpyridine hydrochloride a) 2,3-Dimethyl-4-(3-hydroxypropylthio)pyridine-N-oxide 6 g (60% strength) NaH are added in portions to 50 ml of dry N-methylpyrrolidone (NMP), the mixture is stirred for 15 min., 9.5 g (0.11 mol) of 3-hydroxypropyl mercaptan are metered in in the course of 20 min. and the mixture is again stirred for 30 min. until evolution of gas has ended. A solution of 14.4 g (0.1 mol) of 4-chloro-2,3-dimethylpyridine-N-oxide in 100 ml of NMP is then added dropwise in the course of 20 min., and the reaction mixture is stirred for 1 h at room temperature, then for 1 h at 70° C. and after that for a further 1 h at 100° C.

After reaction has ended, the mixture is allowed to cool, and is diluted with 500 ml of water and extracted 4 times with 300 ml of dichloromethane each time. The combined organic phases are washed with water, dried over magnesium sulfate and concentrated and the residue is crystallized from toluene. After recrystallization from methanol/toluene, the title compound is obtained as a beige solid of m.p. 106–107° C. (sublimes): yield: 68% of theory.

b) 2-Hydroxymethyl-4-(3-hydroxyoropylthio)-3-methylpyridine

The yellow oil obtained under a) is dissolved in 100 ml of acetic anhydride, and the mixture is stirred for 2 h at 100° C. After concentration in vacuo, the brown, oily residue is distilled in a bulb tube distillation apparatus and reacted further without purification.

The oily distillate is heated at reflux temperature with stirring for 2 h in 100 ml of 2 n sodium hydroxide solution and 100 ml of isopropanol, isopropanol is distilled off, the residue is extracted 3 times with 100 ml of dichloromethane each time, and the combined organic phases are washed with water, dried over potassium carbonate and concentrated in vacuo. 5.0 g of 2-hydroxymethyl-4-(3-hydroxypropylthio)-3-methylpyridine are obtained, which is reacted further without purification. From isopropanol, using conc. hydrochloric acid, a monohydrochloride of the title compound can be prepared; m.p. 188–190° C. (dec.).

c) 2-Chloromethyl-4-(3-chloropropylthio)-3-methylpyridine hydrochloride 5.0 g of the oil from b) are dissolved in dichloromethane (100 ml), 4 equivalents of thionyl chloride are added dropwise and the mixture is stirred at room temperature for 20 h. It is concentrated completely and 4.5 g of the title compound are obtained as an oily, gradually crystallizing residue. Crystallization from isopropanol/diisopropyl ether yields the title compound as a colorless solid; m.p. 142–144° C. (dec.).

B1. 2-{[[4-(2-Chloroethylthio)-3-methyl-2-pyridinyl]-methyl]thio}-1H-benzimidazole According to the procedure indicated in Example A1, reaction of 2-mercapto-1H-benzimidazole with 4-(2-chloroethylthio)-2-chloromethyl-3-methylpyridine hydrochloride and NaOH gives, after crystallization from ethyl acetate, the title compound (62% of theory) as a colorless solid of m.p. 178–180° C.

B2. 4-(2-Chloroethylthio)-2-chloromethyl-3-methylpyridine hydrochloride a) 2,3-Dimethyl-4-(2-hydroxyethylthio)pyridine-N-oxide According to the procedure indicated in Example A2.a), reaction of 4-chloro-2,3-dimethylpyridine-N-oxide with 2-mercaptoethanol and sodium hydride gives the title compound as an oily residue which is employed in the subsequent step without further purification.

b) 4-(2-Hydroxyethylthio)-2-hydroxymethyl-3-methylpyridine

According to the procedure indicated in Example A2.b), reaction of the oil obtained under a) with acetic anhydride and subsequent hydrolysis with NaOH gives the title compound as an oily residue which is employed in the subsequent step without further purification.

c) 4-(2-Chloroethylthio)-2-chloromethyl-3-methylpyridine hydrochloride

According to the procedure indicated in Example A2.c), reaction of the oil obtained under b) with thionyl chloride gives the title compound as an oily residue which is employed directly as a solution in ethanol for the reaction with 2-mercaptobenzimidazole.

C1. 2-{[[4-(3-Chloropropylthio)-3-methoxy-2-pyridinyl]methyl]thio}-1H-benzimidazole dihydrochloride 2-Mercapto-1H-benzimidazole (10 g) and 2-chloromethyl-4-(3-chloropropylthio)-3-methoxypyridine hydrochloride (1 equivalent) are stirred at 80° C. for 5 h in 150 ml of isopropanol and 15 ml of water, the mixture is cooled, and the precipitated solid is filtered off and recrystallized from isopropanol/water. The title compound is obtained as a pale brown powder; m.p. 117–119° C. (dec.); yield: 67% of theory.

C2. 2-Chloromethyl-4-(3-chloropropylthio)-3-methoxypyridine hydrochloride

According to the procedure described in Example A2.a), b) and c), starting from 4-chloro-3-methoxy-2-methylpyridine-N-oxide the title compound is obtained as a slowly crystallizing oil which is directly reacted further.

D1. 2-{[[4-(3-Chloropropylthio)-3-methyl-2-pyridinyl]methyl]thio}-1H-imidazo[4.5-b]pyridine dihydrochloride According to the procedure described in Example C1., the reaction of 2-mercapto-1H-imidazo[4,5-b]pyridine with 2-chloromethyl-4-(3-chloropropylthio)-3-methylpyridine hydrochloride gives the title compound as a colorless powder; m.p. 186–188° C.; yield: 88% of theory.

E1. 2-{[[4-(3-Chloropropylthio)-3-methyl-2-pyridinyl]methyl]thio}-5-fluoro-1H-benzimidazole According to the procedure indicated in Example A1., reaction of 5-fluoro-2-mercapto-1H-benzimidazole with 4-(2-chloroethylthio)-2-chloromethyl-3-methylpyridine hydrochloride and NaOH gives, after crystallization from isopropanol, the title compound (94% of theory) as a colorless solid of m.p. 188–191° C.

F1. 2-{[[4-(3-Chloropropylthio)-3-methyl-2-pyridinyl]methyl]thio}-5,6-difluoro-1H-benzimidazole dihydrochloride According to the procedure indicated in Example A1., reaction of 5,6-difluoro-2-mercapto-1H-benzimidazole with 4-(2-chloroethylthio)-2-chloromethyl-3-methylpyridine hydrochloride and NaOH gives, after crystallization from ethyl acetate, the title compound (90% of theory) as a colorless solid of m.p. 205° C.

G1. 2-{[[4-(3-Chloropropylthio)-3-methyl-2-pyridinyl]methyl]thio}-5-fluoro-6-methoxy-1H-benzimidazole dihydrochloride According to the procedure indicated in Example A1., reaction of 5-fluoro-6-methoxy-2-mercapto-1H-benzimidazole with 4-(2-chloroethylthio)-2-chloromethyl-3-methylpyridine hydrochloride and NaOH gives, after crystallization from ethyl acetate, the title compound (96% of theory) as a colorless solid of m.p. 203–205° C.

Commercial Utility

The excellent activity of compounds of the formula I and their salts against Helicobacter bacteria permits their use in human medicine as active compounds for the treatment of diseases which are based on Helicobacter bacteria.

The invention therefore further relates to a method for the treatment of mammals, in particular humans, who are suffering from diseases which are based on Helicobacter bacteria. The method comprises administering to the sick individual a therapeutically effective and pharmacologically tolerable amount of one or more compounds of the formula I and/or their pharmacologically tolerable salts.

The invention additionally relates to the compounds of the formula I and their pharmacologically tolerable salts for use in the treatment of diseases which are based on Helicobacter bacteria.

The invention likewise includes the use of compounds of the formula I and their pharmacologically tolerable salts in the production of medicaments which are employed for the control of those diseases which are based on Helicobacter bacteria.

The invention further relates to medicaments for the control of Helicobacter bacteria, which contain one or more compounds of the general formula I and/or their pharmacologically tolerable salts.

Of the Helicobacter strains against which the compounds of the formula I have proven effective, the strain Helicobacter pylori may be mentioned in particular.

The medicaments are prepared by methods known per se, with which the person skilled in the art is familiar. As medicaments, the pharmacologically active compounds of the formula I and their salts (=active compounds) are either employed as such, or preferably in combination with suitable pharmaceutical auxiliaries, e.g. in the form of tablets, coated tablets, capsules, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, tablet auxiliaries and other active compound excipients, for example, antioxidants, dispersants, emulsifiers, anti-foams, flavor corrigents, preservatives, solubilizers, colorants or permeation promoters and complexing agents (e.g. cyclodextrins) can be used.

The active compounds can be administered, for example, parenterally (e.g. intravenously) or, in particular, orally.

In general, in human medicine the active compounds are administered in a daily dose of approximately 0.2 to 50, preferably 1 to 30, mg/kg of body weight, if appropriate in the form of several, preferably 2 to 6, individual doses to achieve the desired result.

In this connection, it is particularly to be mentioned as an essential aspect of the invention that the compounds of the formula I in which n is the number 0 prove to be effective against Helicobacter bacteria even on administration of those doses which are below the doses which had to be employed to achieve an inhibition of gastric acid secretion sufficing for therapeutic purposes.

Compounds of the formula I in which n is the number 1 also have—beside their activity against Helicobacter bacteria—a marked gastric acid secretion-inhibiting action. Accordingly, these compounds can also be employed for the treatment of those diseases which are based on increased gastric acid secretion.

The compounds according to the invention can also be administered in fixed or free combination together with a substance neutralizing gastric acid and/or inhibiting gastric acid secretion and/or with a substance suitable for the classical control of Helicobacter pylori.

Substances neutralizing gastric acid which may be mentioned are, for example, sodium hydrogencarbonate or other antacids (such as aluminum hydroxide, magnesium aluminate or magaldrate). Substances inhibiting gastric acid secretion which may be mentioned are, for example, H$_2$ blockers (e.g. cimetidine, ranitidine), H$^+$/K$^+$ ATPase inhibitors (e.g. lansoprazole, omeprazole or in particular pantoprazole) as well as so-called peripheral anticholinergics (e.g. pirenzepine, telenzepine).

Substances suitable for the classical control of Helicobacter pylori which may be mentioned are, in particular, substances having antimicrobial activity such as, for example, penicillin G, gentamycin, erythromycin, nitrofurazone, tinidazole, nitrofurantoin, furazolidone, metronidazole and, in particular, amoxycillin, or alternatively also bismuth salts such as, for example, bismuth citrate.

Biological Investigations

The compounds of the formula I were investigated with respect to their activity against Helicobacter pylori following the methodology described by Tomoyuki Iwahi et al. (Antimicrobial Agents and Chemotherapy, 1991, 490–496) using Columbia agar (Oxoid) and with a growth period of 4 days. For the compounds investigated, the approximate MIC 50 values listed in Table A which follows resulted here (the numbers of the compounds indicated correspond to the example numbers in the description).

TABLE A

| Compound No. | Approx. MIC 50 (µg/ml) |
|---|---|
| 1 | ≦0.5 |
| 2 | ≦0.5 |
| 3 | ≦0.5 |
| 4 | ≦0.5 |
| 5 | ≦0.5 |
| 6 | ≦0.5 |
| 7 | ≦0.5 |
| 8 | ≦0.5 |
| 9 | ≦0.5 |
| 10 | ≦0.5 |
| 11 | ≦0.5 |

FORMULA SHEET 1

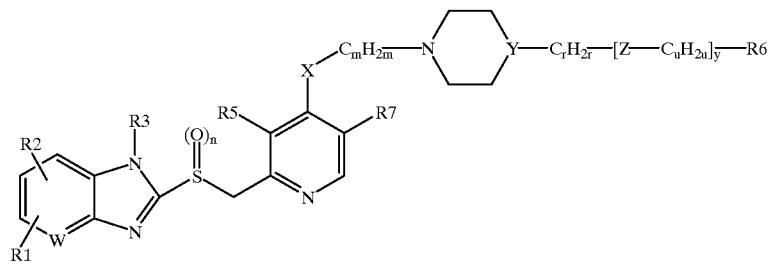

(I)

FORMULA SHEET 2

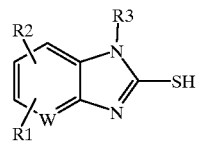

(II)

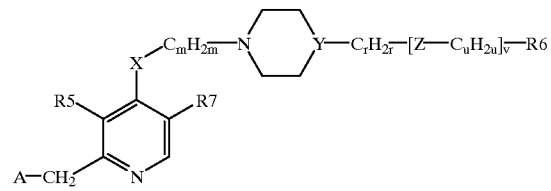

(III)

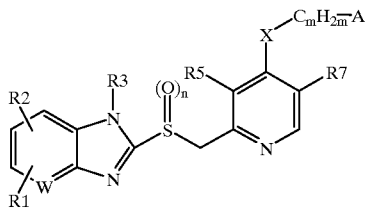

(IV)

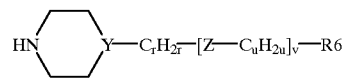

(V)

FORMULA SHEET 3

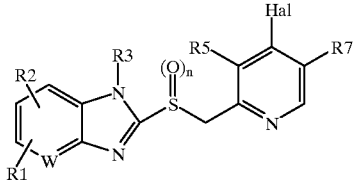
(VI)

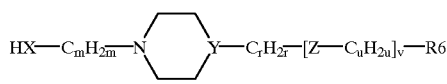
(VII)

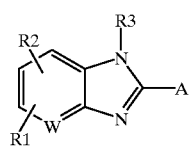
(VIII)

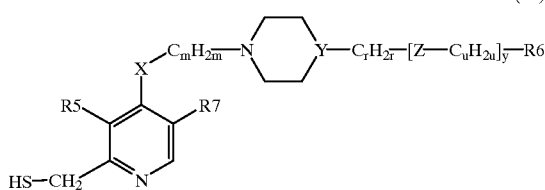
(IX)

We claim:
1. A compound of the formula I

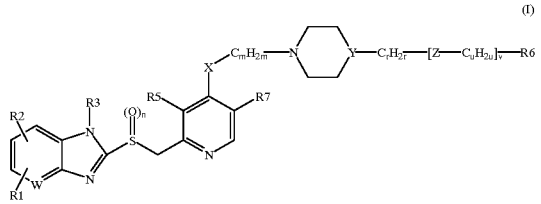
(I)

in which
R1 is hydrogen, 1–4C-alkyl, 1–4C-alkoxy or halogen,
R2 is hydrogen, 1–4C-alkyl, 1–4C-alkoxy, halogen or trifluoromethyl,
R3 is hydrogen, 1–4C-alkyl, R4-substituted 1–4C-alkyl, 1–4C-alkylcarbonyl, 2–4C-alkenylcarbonyl, halogen-1–4C-alkylcarbonyl, N(R14)R15-1–4C-alkylcarbonyl, di-1–4C-alkylcarbamoyl or 1–4C-alkylsulfonyl,
R4 is hydroxyl, 1–4C-alkoxy, carboxyl, 1–4C-alkoxycarbonyl or —N(R14)R15,
R5 is hydrogen, 1–4C-alkyl or 1–4C-alkoxy,
R6 is an R8- and R9-substituted cyclic system or bicyclic system which is selected from the group consisting of benzene, furan, thiophene, pyrrole, oxazole, isoxazole, thiazole, thiazoline, isothiazole, imidazole, imidazoline, pyrazole, triazole, tetrazole, thiadiazole, thiadiazole-1-oxide, oxadiazole, pyridine, pyridine-N-oxide, pyrimidine, triazine, pyridone, benzimidazole, imidazopyridine; benzothiazole and benzoxazole,
R7 is hydrogen, 1–4C-alkyl or 1–4C-alkoxy,
R8 is hydrogen, 1–4C-alkyl, hydroxyl, 1–4C-alkoxy, halogen, nitro, guanidino, carboxyl, 1–4C-alkoxycarbonyl, R10-substituted 1–4C-alkyl or —N(R11)R12,
R9 is hydrogen, 1–4C-alkyl, hydroxyl, 1–4C-alkoxy, halogen or trifluoromethyl,
R10 is hydroxyl, 1–4C-alkoxy, carboxyl, 1–4C-alkoxycarbonyl or —N(R11)R12, where
R11 is hydrogen, 1–4C-alkyl or —CO—R13 and
R12 is hydrogen or 1–4C-alkyl, or where
R11 and R12, together and including the nitrogen atom to which both are bonded, are a piperidino or morpholino radical,
R13 is hydrogen, 1–4C-alkyl or 1–4C-alkoxy,
R14 is 1–4C-alkyl and
R15 is 1–4C-alkyl, or where
R14 and R15, together and including the nitrogen atom to which both are bonded, are a piperidino or morpholino radical,
W is CH or N,
X is O (oxygen), N-1–4C-alkyl or S (sulfur),
Y is N or CH,
Z is O (oxygen), CO (carbonyl), S (sulfur) or $SO_2$,
m is a number from 2 to 5,
n is the number 0, 1 or 2,
r is a number from 0 to 5,
u is a number from 0 to 3 and
v is the number 0 or 1
or a salt thereof,
where
R6 does not have the meaning of benzene if R5 is hydrogen or 1–4C-alkyl and v is the number 0,
r is not the number 0 if Y is N and Z is O, S or $SO_2$,
Z is not $SO_2$ if u is the number 0 and v is the number 1, and where
R6 is not an N (nitrogen)-bonded cyclic system or bicyclic system if Z is O, S or $SO_2$, v is the number 1 and u is the number 0.
2. A compound of the formula I as claimed in claim 1, in which
R1 is hydrogen, 1–4C-alkoxy or halogen,
R2 is hydrogen or halogen,
R3 is hydrogen, R4-substituted 1–4C-alkyl, N(R14)R15-1–4C-alkylcarbonyl or 1–4C-alkylsulfonyl,
R4 is —N(R14)R15,
R5 is hydrogen, 1–4C-alkyl or 1–4C-alkoxy,
R6 is an R8- and R9-substituted cyclic system or bicyclic system which is selected from the group consisting of benzene, furan, thiophene, thiazole, imidazole, triazole, pyridine, pyrimidine and pyridone,
R7 is hydrogen,
R8 is hydrogen, 1–4C-alkyl, 1–4C-alkoxy, halogen, nitro or R10-substituted 1–4C-alkyl,
R9 is hydrogen, 1–4C-alkyl or fluorine,
R10 is —N(R11)R12, where
R11 is 1–4C-alkyl and
R12 is 1–4C-alkyl, or where
R11 and R12, together and including the nitrogen atom to which both are bonded, are a piperidino or morpholino radical,
R14 is 1–4C-alkyl and
R15 is 1–4C-alkyl, or where R14 and R15, together and including the nitrogen atom to which both are bonded, are a piperidino or morpholino radical, W is CH or N, X is O (oxygen) or S (sulfur), Y is N or CH, Z is O (oxygen), CO (carbonyl), S (sulfur) or $SO_2$, m is a number from 2 to 4, n is the number 0 or 1, r is a number from 0 to 3, u is a number from 0 to 2 and v is the number 0 or 1 or a salt thereof,
where
R6 does not have the meaning of benzene if R5 is hydrogen or 1–4C-alkyl and v is the number 0, r is not the number 0 if Y is N and Z is O, S or $SO_2$, Z is not $SO_2$ if u is the number 0 and v is the number 1, and where R6 is not an N (nitrogen)-bonded cyclic system or bicyclic system if Z is O, S or $SO_2$, v is the number 1 and u is the number 0.

3. A compound of the formula I as claimed in claim 1, in which

R1 is hydrogen,

R2 is hydrogen,

R3 is hydrogen,

R5 is 1–4C-alkyl or 1–4C-alkoxy,

R6 is an R8- and R9-substituted cyclic system or bicyclic system which is selected from the group consisting of benzene, furan, thiophene, thiazole, pyridine and pyrimidine, R7 is hydrogen, R8 is hydrogen, 1–4C-alkyl, halogen or R10-substituted 1–4C-alkyl, R9 is hydrogen, R10 is —N(R11)R12, where R11 is 1–4C-alkyl and R12 is 1–4C-alkyl, W is CH, X is S (sulfur), Y is N or CH, Z is CO (carbonyl) or S (sulfur), m is the number 3, n is the number 0, r is a number from 0 to 3, u is the number 0 and v is the number 0 or 1 or a salt thereof,
where
R6 does not have the meaning of benzene if R5 is 1–4C-alkyl and v is the number 0,
and where
r is not the number 0 if Y is N and Z is S.

4. A compound of the formula I as claimed in claim 1, in which v is the number 1, Z is CO (carbonyl), r is the number 0 and u is the number 0.

5. A compound of the formula I as claimed in claim 1, in which v is the number 1, Z is S (sulfur), Y is N, r is the number 2 or 3 and u is the number 0 or 1.

6. A compound of the formula I as claimed in claim 1, in which v is the number 0 and r is a number from 0 to 3.

7. A compound of the formula I as claimed in claim 1, in which R5 is 1–4C-alkoxy and R6 is R8- and R9-substituted benzene.

8. A method for treating a mammal afflicted with a disease based on Helicobacter bacteria which comprises administering to the mammal an effective amount of a compound of claim 1 or of a pharmacologically acceptable salt thereof.

9. In a method for compounding a medicament composition comprising a suitable pharmaceutical auxiliary in combination with active ingredient for treating a disease based on Helicobacter bacteria, the improvement wherein the active ingredient is a compound of claim 1 or a pharmacologically acceptable salt thereof.

10. In a medicament composition comprising a suitable pharmaceutical auxiliary in combination with an effective amount of active ingredient for treating a disease based on Helicobacter bacteria, the improvement wherein the active ingredient is a compound of claim 1 or a pharmacologically acceptable salt thereof.

11. A method of controlling Helicobacter bacteria which comprises applying to the bacteria an effective amount of a compound of claim 1 or of a salt thereof.

12. A process for preparing a compound of formula I as claimed in claim 1 or a salt thereof, which comprises reacting a compound of formula IV

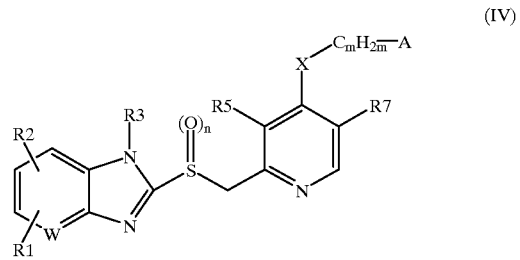

(IV)

in which W, R1, R2, R3, R5, R7, X and m have meanings specified in claim 1, n is the number 0 and A is a suitable leaving group, with a compound of formula V

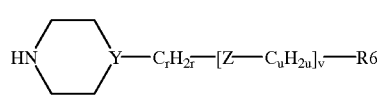

(V)

in which R6, Y, Z, r, u and v have meanings specified in claim 1, and (when a compound of formula I with n=1 or 2 and/or Z=$SO_2$ is the desired final product) oxidizing the compound obtained when n=0 and/or Z=S and optionally converting the obtained compound into a corresponding salt or converting an obtained salt into a corresponding free compound.

13. A compound of formula I as claimed in claim 1 in which Y is CH, or a salt thereof.

14. A compound of formula I as claimed in claim 1 in which v is 1, or a salt thereof.

15. A compound of formula I as claimed in claim 1 in which r is 0, or a salt thereof.

16. A compound of formula I as claimed in claim 1 in which X is N-1–4C-alkyl, or a salt thereof.

* * * * *